(12) United States Patent
Gac et al.

(10) Patent No.: US 8,592,413 B2
(45) Date of Patent: Nov. 26, 2013

(54) THERAPEUTIC SUBSTITUTED CYCLOPENTANES

(75) Inventors: Todd Gac, Santa Ana, CA (US); David W. Old, Irvine, CA (US)

(73) Assignee: Allergan, Inc., Irvine, CA (US)

( * ) Notice: Subject to any disclaimer, the term of this patent is extended or adjusted under 35 U.S.C. 154(b) by 197 days.

(21) Appl. No.: 12/992,160

(22) PCT Filed: May 11, 2009

(86) PCT No.: PCT/US2009/043480
§ 371 (c)(1),
(2), (4) Date: Mar. 30, 2011

(87) PCT Pub. No.: WO2009/140205
PCT Pub. Date: Nov. 19, 2009

(65) Prior Publication Data
US 2011/0172299 A1 Jul. 14, 2011

Related U.S. Application Data

(60) Provisional application No. 61/053,354, filed on May 15, 2008.

(51) Int. Cl.
*A61K 31/5355* (2006.01)
*C07D 413/12* (2006.01)

(52) U.S. Cl.
USPC ........................ 514/231.5; 544/146

(58) Field of Classification Search
USPC ............... 514/448, 231.5; 549/71; 544/146
See application file for complete search history.

(56) References Cited

U.S. PATENT DOCUMENTS

| | | | |
|---|---|---|---|
| 3,980,700 | A | 9/1976 | Miyano |
| 4,119,727 | A | 10/1978 | Buendia et al. |
| 4,403,100 | A | 9/1983 | Morton, Jr. |
| 5,889,052 | A | 3/1999 | Klimko et al. |
| 6,426,359 | B1 | 7/2002 | Cameron et al. |
| 6,437,146 | B1 | 8/2002 | Hattori et al. |
| 6,710,072 | B2 | 3/2004 | Burk et al. |
| 7,323,591 | B2 | 1/2008 | Old et al. |
| 7,405,240 | B2 | 7/2008 | Old et al. |
| 7,429,669 | B2 | 9/2008 | Old et al. |
| 2007/0129552 | A1 | 6/2007 | Donde et al. |

FOREIGN PATENT DOCUMENTS

| | | |
|---|---|---|
| CA | 2088161 | 7/1991 |
| GB | 2108960 | 5/1983 |
| JP | 2001-163779 | 6/2001 |
| WO | WO 2008/008700 | 5/1983 |
| WO | WO 92/02495 | 2/1992 |
| WO | WO 98/27976 | 7/1998 |
| WO | WO 98/58911 | 12/1998 |
| WO | WO9854180 | 12/1998 |
| WO | WO 02/26704 | 4/2002 |
| WO | WO 03/074483 | 9/2003 |
| WO | WO 2004-089411 | 10/2004 |
| WO | WO 2008/008660 | 1/2008 |

OTHER PUBLICATIONS

Francis A. Carey, Organic Chemistry, McGraw-Hill Book Company: New York, 1987, pp. 11-13.
Prodrugs and Drug Delivery Systems, which is a chapter in Richard B. Silverman, *Organic Chemistry of Drug Design and Drug Action*, 2d Ed., Elsevier Academic Press: Amsterdam, 2004, pp. 496-557.
Larsen, Anderson, Tundel and Buchwald: Synlett 2006, 2941-2946.
Patani, George A. Bioisosterism: A rational approach in drug design. Chem. Rev. 96 (1996) 3147-3176.
Stella, Valentino J, Expert Opinion of Therapeutic Patents, Prod rugs as therapeutics, 200414(3): 277-280 (2004).
Wolff et al. (Burger's Medicinal Chemistry, 5th Ed., vol. 1, pp. 975-977, 1994.
Testa, Bernard, Biochemical Pharmacology, Prodrug Research: futile or fertile? 68 (2004) 2097-210.
Ettmayer, Peter, Medicinal Chemistry, Lessons Learned from Marketed and Investigational Prodrugs, 47(10) (2004) 2394-2404.
Kwon, Younggil. Handbook of Essential Pharmacokinetics, Pharmacodynamics and Drug Metabolism for Industrial Scientists., Jun. 24, 2001. p. 213.
"Metabolomics." Retrieved online via the Internet [Jun. 17, 2008] URL: www.en.wikipedia.org/wiki/Metabolomics.
Baxter, Anthony D., et al., *Synthesis and Use of 7-Substituted Norbomadienes for the Preparation of Prostglandins and Prostanoids*, 1986, 889, J. Chem. Soc. Perkin.
Dragoli, Dean R., et al., *Parallel Synthesis of Prostaglandin E1 Analogues*, 1999, 534-539, J. Comb. Chem.
Tomoskozi, Tetrahedron Letters No. 6, pp. 581-584, 1978. Pergamon Press. Printed in Great Britain.
Vilmos Simonidesz, et al.; "Addition of Thallium Triacetate to PFG20c Methyl Ester and Re\ated Compounds in Acetic Acid. Nuclear Magnetic Resonance Spectral Study of Novel Dioxatricyclic and Oxabicyclic Products" J .C.S. Perkin I ; pp. 2572-2580; 1980.
Cory Jacs, "Protection of Hydroxyl Groups as tert-Butyldimethylsilyl Derivatives" Journal of the American Chemical Society / 94:17 / Aug. 23, 1972.

*Primary Examiner* — Taofiq A Solola
(74) *Attorney, Agent, or Firm* — Lorenz Siddiqi; Allergan, Inc.

(57) ABSTRACT

Disclosed herein are compounds represented by a formula: Therapeutic methods, compositions, and medicaments related thereto are also disclosed.

(I)

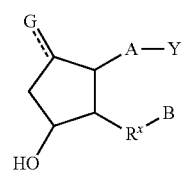

5 Claims, No Drawings

THERAPEUTIC SUBSTITUTED CYCLOPENTANES

CROSS-REFERENCE

This is a national stage application under 35 U.S.C. §371 of PCT patent application PCT/US09/43480, filed on May 11 2009, which claims the benefit of U.S. Provisional Patent Application 61/053,354, filed on May 15, 2008, each of which is hereby incorporated by reference in its entirety.

DESCRIPTION OF THE INVENTION

Disclosed herein are compounds represented by a formula:

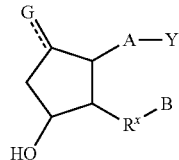

wherein a dashed line represents the presence or absence of a bond;

Y is $C_{0-14}H_{1-30}O_{1-4}S_{0-2}N_{0-4}P_{0-1}$ and is: an organic acid functional group, or an amide or ester thereof; hydroxymethyl or an ether thereof; or a tetrazolyl functional group;

A is —$(CH_2)_6$—, cis —$CH_2CH$=$CH$—$(CH_2)_3$—, or —$CH_2C$≡$C$—$(CH_2)_3$—, wherein 1 or 2 carbon atoms may be replaced by S or O; or A is —$(CH_2)_m$—Ar—$(CH_2)_o$—, wherein the sum of m and o is 1, 2, 3, or 4, and wherein 1 —$CH_2$— may be replaced by S or O, and 1 —$CH_2$—$CH_2$— may be replaced by —$CH$=$CH$— or —$C$≡$C$—;

Ar is aryl of a formula $C_{3-10}H_{0-23}N_{0-4}O_{0-4}S_{0-4}F_{0-5}Cl_{0-3}Br_{0-3}I_{0-3}$, G is —H, —OH, =O, —Cl, —F, —CN;

$R^x$ is —$(CH_2)_3$—, —$CH$=$CHCH_2$—, —$CH$=$C$=$CH$—, —$CH_2OCH_2$—, $CH_2SCH_2$—, —$CH_2NHCH_2$—, —$(CH_2)_2O$—, —$(CH_2)_2S$—, or —$(CH_2)_2NH$—; and B is aryl of a formula $C_{3-20}H_{0-45}N_{0-4}O_{0-4}S_{0-4}F_{0-5}Cl_{0-3}Br_{0-3}I_{0-3}$.

Also disclosed herein are compounds represented by a formula:

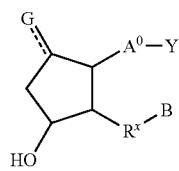

wherein a dashed line represents the presence or absence of a bond;

Y is $C_{0-14}H_{1-30}O_{1-4}S_{0-2}N_{0-4}P_{0-1}$ and is: an organic acid functional group, or an amide or ester thereof; hydroxymethyl or an ether thereof; or a tetrazolyl functional group;

$A^0$ is —$(CH_2)_m$—Ar—$(CH_2)_o$—, wherein the sum of m and o is 1, 2, 3, or 4, and wherein 1 —$CH_2$— may be replaced by S or O, and 1 —$CH_2$—$CH_2$-may be replaced by —$CH$=$CH$— or —$C$≡$C$—;

Ar is aryl of a formula $C_{3-10}H_{0-23}N_{0-4}O_{0-4}S_{0-4}F_{0-5}Cl_{0-3}Br_{0-3}I_{0-3}$, G is —H, —OH, =O, —Cl, —F, —CN;

$R^x$ is —$(CH_2)_3$—, —$CH$=$CHCH_2$—, —$CH$=$C$=$CH$—, —$CH_2OCH_2$—, $CH_2SCH_2$—, —$CH_2NHCH_2$—, —$(CH_2)_2O$—, —$(CH_2)_2S$—, or —$(CH_2)_2NH$—; and B is aryl of a formula $C_{3-20}H_{0-45}N_{0-4}O_{0-4}S_{0-4}F_{0-5}Cl_{0-3}Br_{0-3}I_{0-3}$.

Also disclosed herein are compounds represented by a formula:

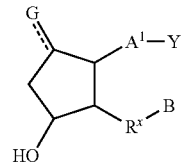

wherein a dashed line represents the presence or absence of a bond;

Y is $C_{0-14}H_{1-30}O_{1-4}S_{0-2}N_{0-4}P_{0-1}$ and is: an organic acid functional group, or an amide or ester thereof; hydroxymethyl or an ether thereof; or a tetrazolyl functional group;

$A^1$ is —$(CH_2)_6$—, cis —$CH_2CH$=$CH$—$(CH_2)_3$—, or —$CH_2C$≡$C$—$(CH_2)_3$—, wherein 1 or 2 carbon atoms may be replaced by S or O;

G is —H, —OH, =O, —Cl, —F, —CN;

$R^x$ is —$(CH_2)_3$—, —$CH$=$CHCH_2$—, —$CH$=$C$=$CH$—, —$CH_2OCH_2$—, $CH_2SCH_2$—, —$CH_2NHCH_2$—, —$(CH_2)_2O$—, —$(CH_2)_2S$—, or —$(CH_2)_2NH$—; and B is aryl of a formula $C_{3-20}H_{0-45}N_{0-4}O_{0-4}S_{0-4}F_{0-5}Cl_{0-3}Br_{0-3}I_{0-3}$.

These compounds are useful for reducing intraocular pressure, treating glaucoma or intraocular pressure, growing hair, or improving the appearance of hair. Growing hair includes increasing the length or radius of individual hairs as well as increasing the number of hairs present in a given area. Improving the appearance of hair includes improving the color, such as darkening, or improving its gloss, shine, or other properties related to the reflection or dispersion of light.

Unless otherwise indicated, reference to a compound should be construed broadly to include pharmaceutically acceptable salts, prodrugs, tautomers, alternate solid forms, non-covalent complexes, and combinations thereof, of a chemical entity of a depicted structure or chemical name.

Any description of a compound made herein is not intended to encompass compounds having structural features that violate the basic principles of chemistry such as containing an atom having too many or too few electrons in its valence shell (see Francis A. Carey, Organic Chemistry, McGraw-Hill Book Company: New York, 1987, pp. 11-13). It is also not intended to encompass compounds that are too reactive or otherwise too unstable to be useful as described herein. For example, it is not intended to encompass compounds that cannot either: 1) be put into a bottle with an excipient for subsequent use in treating a mammal as disclosed herein, or 2) be put into a bottle as a salt or a prodrug of the compound with an excipient for subsequent use in treating a mammal as disclosed herein.

Unless otherwise indicated, if a term is used to describe more than one structural feature of the compounds disclosed herein, it should be assumed that the term has the same meaning for all of those features. Similarly, a subgroup of that term applies to every structural feature described by that term.

Unless stereochemistry is explicitly and unambiguously depicted, a structure is intended to include every possible stereoisomer, both pure or in any possible mixture.

"Treat," "treating," or "treatment" refer to the use of a compound, composition, therapeutically active agent, or drug in the diagnosis, cure, mitigation, treatment, or prevention of disease or other undesirable condition.

A pharmaceutically acceptable salt is any salt of the parent compound that is suitable for administration to an animal or human. A pharmaceutically acceptable salt also refers to any salt which may form in vivo as a result of administration of an acid, another salt, or a prodrug which is converted into an acid or salt. A salt comprises one or more ionic forms of the compound, such as a conjugate acid or base, associated with one or more corresponding counter-ions. Salts can form from or incorporate one or more deprotonated acidic groups (e.g. carboxylic acids), one or more protonated basic groups (e.g. amines), or both (e.g. zwitterions).

A prodrug is a compound which is converted to a therapeutically active compound after administration. For example, conversion may occur by hydrolysis of an ester group or some other biologically labile group. Prodrug preparation is well known in the art. For example, "Prodrugs and Drug Delivery Systems," which is a chapter in Richard B. Silverman, *Organic Chemistry of Drug Design and Drug Action,* 2d Ed., Elsevier Academic Press: Amsterdam, 2004, pp. 496-557, provides further detail on the subject. In particular, alkyl esters having such as methyl, ethyl, isopropyl, and the like are contemplated. Also contemplated are prodrugs containing a polar group such as hydroxyl or morpholine. Examples of such prodrugs include compounds containing the moieties —$CO_2(CH_2)_2OH$,

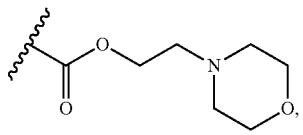 [SMILES: *C(=O)OCCN1CCOCC1]

and the like.

Tautomers are isomers that are in rapid equilibrium with one another. For example, tautomers may be related by transfer of a proton, hydrogen atom, or hydride ion.

Alternate solid forms are different solid forms than those that may result from practicing the procedures described herein. For example, alternate solid forms may be polymorphs, different kinds of amorphous solid forms, glasses, and the like.

Non-covalent complexes are complexes that may form between the compound and one or more additional chemical species. In these complexes, the compound and the additional chemical species have attractive interactions that are not covalent bonds. Examples include solvates, hydrates, charge transfer complexes, and the like.

An organic acid functional group is an acidic functional group on an organic molecule. For example, organic acid functional groups may comprise an oxide of carbon, sulfur, or phosphorous, such as a carboxylic acid, sulfonic acid, or phosphonic acid functional group.

An amide is a functional group where an —OH of an organic acid is replaced by a nitrogen atom which is directly attached to: 1) two carbon atoms, 2) two hydrogen atoms, 3) a carbon atom and a hydrogen atom, or 4) a sulfur atom of a sulfonyl (—$SO_2$—) and hydrogen atom.

An ester is a functional group where an —OH of an organic acid is replaced by an oxygen atom which is directly attached to a carbon atom.

The structures below depict examples different organic acid functional groups and their associated amides and esters.

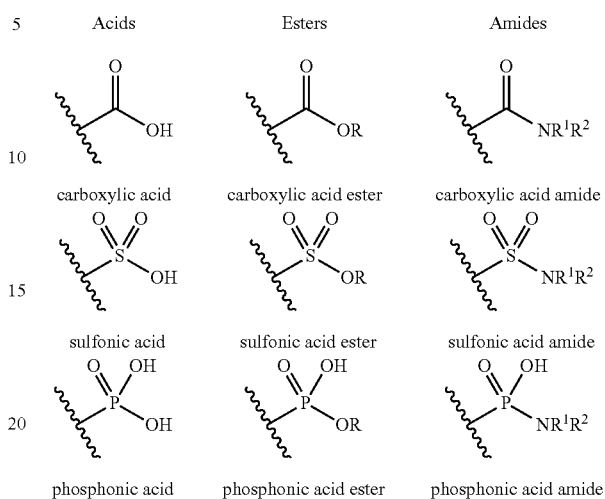

In these examples, R could be alkyl, another hydrocarbyl, or a species such as —$CH_2CH_2OH$. $R^1$ and $R^2$ could be hydrogen, alkyl, another hydrocarbyl, or alkyl sulfonyl (i.e. —$SO_2$-alkyl).

Hydrocarbyl is a moiety consisting only of hydrogen atoms and carbon atoms. Examples include:
1. alkyl, which is hydrocarbyl that contains no double or triple bonds, such as:
   a. linear alkyl, e.g. methyl, ethyl, n-propyl, n-butyl, n-pentyl, n-hexyl, etc.,
   b. branched alkyl, e.g. iso-propyl, t-butyl and other branched butyl isomers, branched pentyl isomers, etc.,
   c. cycloalkyl, e.g. cyclopropyl, cyclobutyl, cyclopentyl, cyclohexyl, etc., and
   d. combinations of linear, branched, and/or cycloalkyl;
   $C_{1-3}$ alkyl is alkyl having from 1 to 3 carbon atoms such as methyl, ethyl, propyl, isopropyl, cyclopropyl, etc.
   $C_{1-6}$ alkyl is alkyl having from 1 to 6 carbon atoms such as methyl, ethyl, propyl isomers, butyl isomers, pentyl isomers, hexyl isomers, cyclopropyl, cyclobutyl, cyclopentyl, cyclohexyl, etc.
   $C_{1-10}$ alkyl is alkyl having from 1 to 10 carbon atoms.
2. alkenyl, which is hydrocarbyl having 1 or more double bonds, including linear, branched, or cycloalkenyl;
3. alkynyl, which is hydrocarbyl having 1 or more triple bonds, including linear, branched, or cycloalkynyl;
4. unsubstituted phenyl, naphthyl, etc.; and
5. combinations of alkyl, alkenyl, akynyl; and unsubstituted phenyl, naphthyl, etc.

Hydroxyalkyl is alkyl-OH. For example, hydroxymethyl is —$CH_2OH$.

$C_{1-6}$ hydroxyalkyl is hydroxyalkyl having from 1 to 6 carbon atoms, such as hydroxymethyl, hydroxyethyl isomers, hydroxypropyl isomers, hydroxybutyl isomers, hydroxypentyl isomers, hydroxyhexyl isomers, etc.

$C_{1-10}$ hydroxyalkyl is hydroxyalkyl having from 1 to 10 carbon atoms.

An ether is a moiety comprising an oxygen attached to two different carbon atoms. For example, an ether of hydroxymethyl is —$CH_2$—O-hydrocarbyl. Another example is —O-alkyl.

$C_{1-3}$ —O-alkyl is —O-alkyl having 1, 2, or 3 carbon atoms such as —O-methyl, —O-ethyl, —O—$C_3H_7$.

C$_{1-10}$ —O-allkyl is —O-alkyl having from 1-10 carbon atoms.

C$_{1-3}$ —S-alkyl is —S-alkyl having 1, 2, or 3 carbon atoms such as —S-methyl, —S-ethyl, —S—C$_3$H$_7$.

C$_{1-10}$ —S-allkyl is —S-alkyl having from 1-10 carbon atoms.

Acyl is

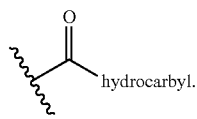

C$_{1-10}$ acyl is acyl having from 1-10 carbon atoms, such as formyl, acetyl, propionyl, butyryl, pentanoyl, hexanoyl, benzoyl, etc.

A tetrazolyl functional group has one of the tautomeric ring structures below:

The hydrogen on either tautomeric form may be replaced by a substituent as well. These moieties are also considered to be tetrazolyl functional groups.

Aryl is an unsubstituted or substituted aromatic ring or aromatic ring system. The ring or ring system atoms could all be carbon. Alternatively, heteroaryl, a subgenus of aryl, has one or more oxygen, sulfur, or nitrogen atoms in the ring or ring system.

Monocyclic aryl is aryl having only one ring.

Unsubstituted aryl refers to aryl with no substituents. Substituted aryl refers to aryl with one or more substituents. If a group is indicated as "aryl" the bond or bonds to that group must directly attach to a carbon atom of an aromatic ring, and not to a substituent.

Any group may be a substituent subject to any restrictions placed upon the moiety that the aryl group is a part of. Examples of substituents include:

hydrocarbyl, as described above alkyl-CN, such as —CH$_2$—CN, —(CH$_2$)$_2$—CN; —(CH$_2$)$_3$—CN, and the like;

Hydroxy, —OH hydroxyalkyl, i.e. alkyl-OH, such as hydroxymethyl, hydroxyethyl, and the like;

ether substituents, including —O-alkyl, alkyl-O-alkyl, and the like;

thioether substituents, including —S-alkyl, alkyl-S-alkyl, and the like;

amine substituents, including —NH$_2$, —NH-alkyl, —N-alkyl$^1$alkyl$^2$ (i.e., alkyl$^1$ and alkyl$^2$ are the same or different, and both are attached to N), alkyl-NH$_2$, alkyl-NH-alkyl, alkyl-N-alkyl$^1$alkyl$^2$, and the like;

aminoalkyl, meaning alkyl-amine, such as aminomethyl (—CH$_2$-amine), aminoethyl, and the like;

ester substituents, including —CO$_2$-alkyl, —CO$_2$-phenyl, etc.;

other carbonyl substituents, including aldehydes; ketones, such as acyl, including, acetyl, propionyl, and benzoyl substituents;

fluorocarbons or hydrofluorocarbons such as —CF$_3$, —CH$_2$CF$_3$, etc.; and other nitrogen containing substituents such as —CN and —NO$_2$, other sulfur containing substitutents such as sulfide, sulfonyl or sulfoxide;

aryl;

combinations of the above are also possible, subject to the constraints defined;

Alternatively, a substituent may be —F, —Cl, —Br, or —I.

The terms imidazolyl, pyrrolyl, furanyl, oxazolyl, thiazolyl, thienyl, pyridinyl, and phenyl refer to both the unsubstituted and substituted versions of the monocyclic aryl rings below.

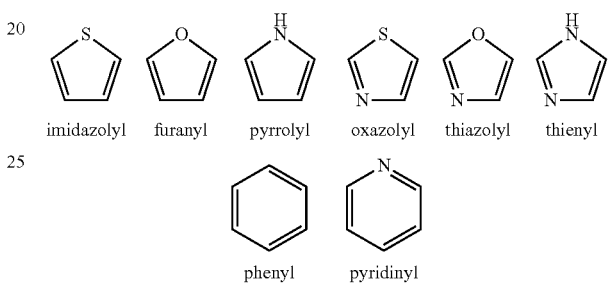

The terms biphenyl, naphthyl, benzothionyl, indolyl, benzofuranyl, benzothiazolyl, benzooxazolyl, quinolinyl, and isoquinolinyl and refer to both the unsubstituted and substituted versions of the bicyclic aryl ring systems below.

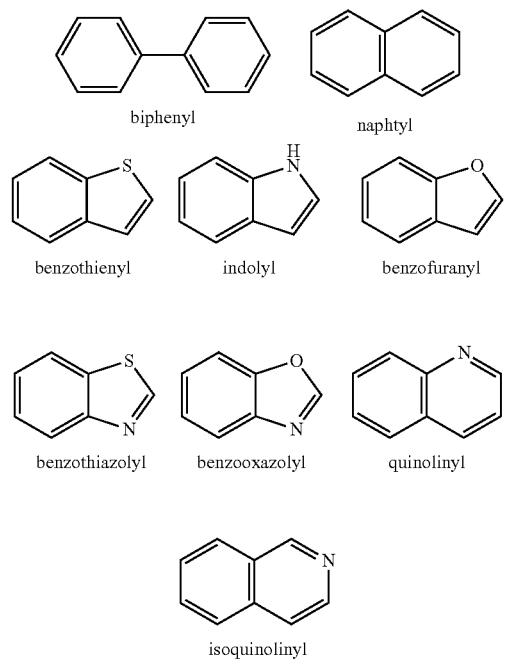

A dashed line in a structure herein represents the presence or absence of a bond. Thus, compounds according to any of the formulas below are possible.

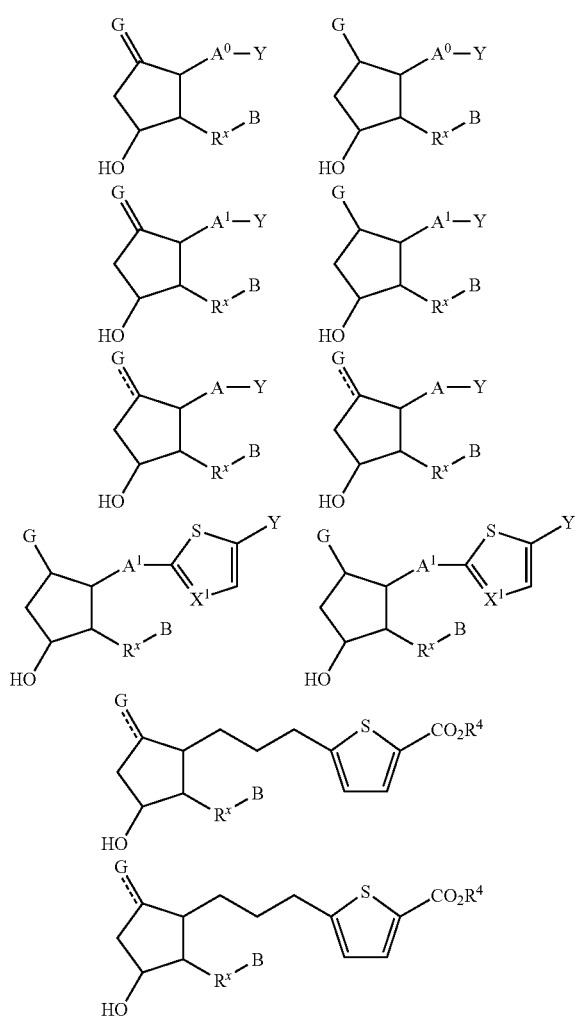

Y is $C_{0-14}H_{1-30}O_{1-4}S_{0-2}N_{0-4}P_{0-1}$ and is: an organic acid functional group, or an amide or ester thereof; hydroxymethyl or an ether thereof; or a tetrazolyl functional group. The formula $C_{0-14}H_{1-30}O_{1-4}S_{0-2}N_{0-4}P_{0-1}$ means that Y consists of from 0-14 carbon atoms, from 1-30 hydrogen atoms, from 1-4 oxygen atoms, from 0-2 sulfur atoms, from 0-4 nitrogen atoms, and from 0-1 phosphorus atoms.

In one embodiment, Y is —$CO_2R^4$, —$CONR^5R^6$, —$CON(CH_2CH_2OH)_2$, —$CONH(CH_2CH_2OH)$, —$CH_2OH$, —$P(O)(OH)_2$, —$CONHSO_2R^4$, —$SO_2NR^5R^6$,

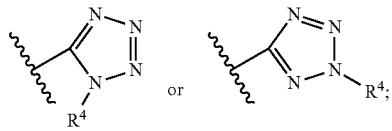

wherein $R^4$, $R^5$ and $R^6$ are independently H, $C_1$-$C_6$ alkyl, $C_{1-6}$ hydroxyalkyl, unsubstituted phenyl, or unsubstituted biphenyl.

In another embodiment, Y is —$CO_2R^4$.

In another embodiment, Y is —$CO_2H$, —$CO_2CH_3$, —$CO_2CH_2CH_3$, or —$CO_2$—$C_3H_7$.

In another embodiment Y is —$CO_2(CH_2)_2OH$ or

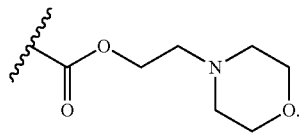 [SMILES: *C(=O)OCCN1CCOCC1]

In another embodiment Y is —$CONR^5R^6$.

A is —$(CH_2)_6$—, cis —$CH_2CH=CH$—$(CH_2)_3$—, or —$CH_2C\equiv C$—$(CH_2)_3$—, wherein 1 or 2 carbon atoms may be replaced by S or O; or A is —$(CH_2)_m$—Ar—$(CH_2)_o$—, wherein the sum of m and o is 1, 2, 3, or 4, and wherein 1 —$CH_2$— may be replaced by S or O, and 1 —$CH_2$—$CH_2$— may be replaced by —$CH=CH$— or —$C\equiv C$—. Ar is aryl of a formula $C_{3-10}H_{0-23}N_{0-4}O_{0-4}S_{0-4}F_{0-5}Cl_{0-3}Br_{0-3}I_{0-3}$.

$A^1$ is —$(CH_2)_6$—, cis —$CH_2CH=CH$—$(CH_2)_3$—, or —$CH_2C\equiv C$—$(CH_2)_3$—, wherein 1 or 2 carbon atoms may be replaced by S or O;

Thus, A or $A^1$ may be —$(CH_2)_6$—, cis —$CH_2CH=CH$—$(CH_2)_3$—, or —$CH_2C\equiv C$—$(CH_2)_3$—.

Alternatively, A or $A^1$ may be a group which is related to one of these three moieties in that any carbon is replaced with S or O. For example, A may be a moiety where S replaces one or two carbon atoms such as one of the following or the like.

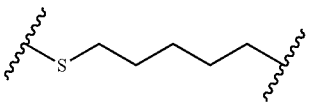
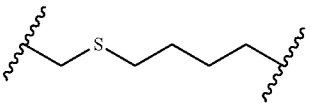
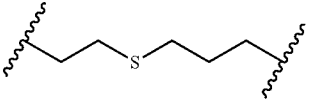
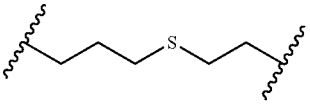
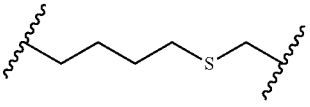
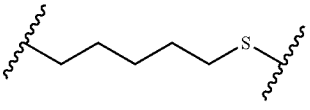
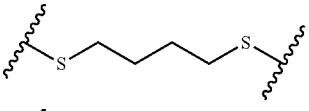
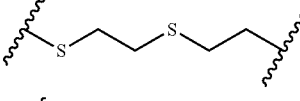

-continued
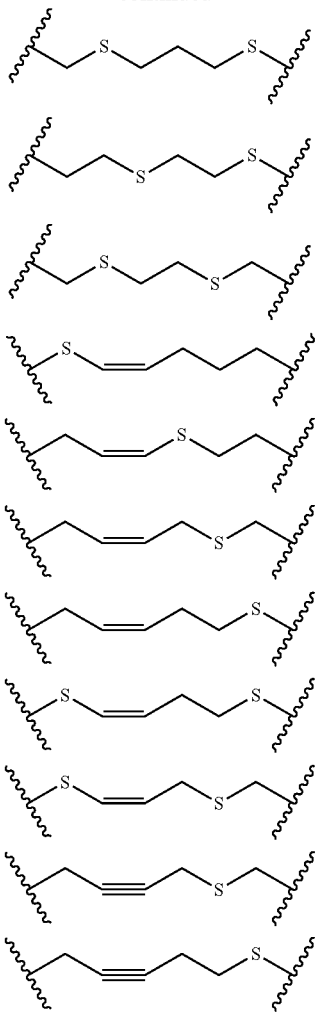
Alternatively, A or A¹ may be a moiety where O replaces one or two carbon atoms such as one of the following or the like.
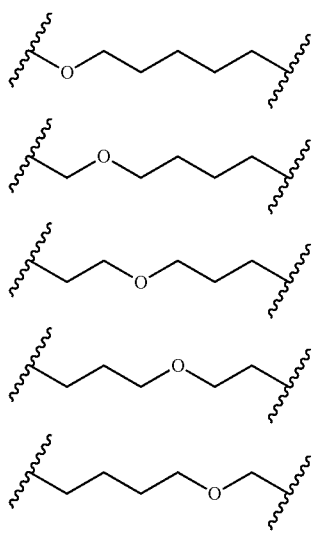
-continued
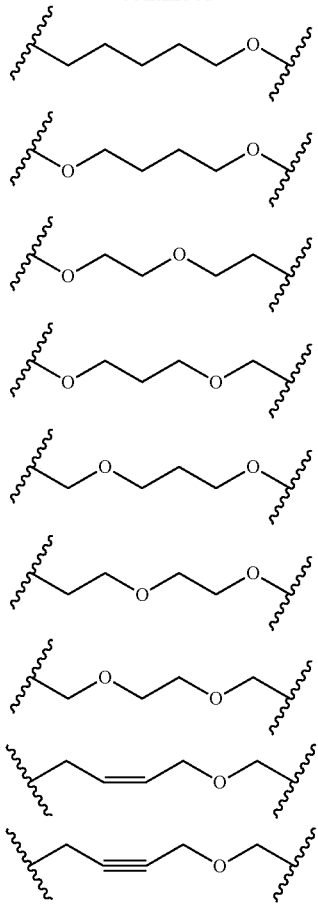
Alternatively, A or A¹ may have an O replacing one carbon atom and an S replacing another carbon atom, such as one of the following or the like.
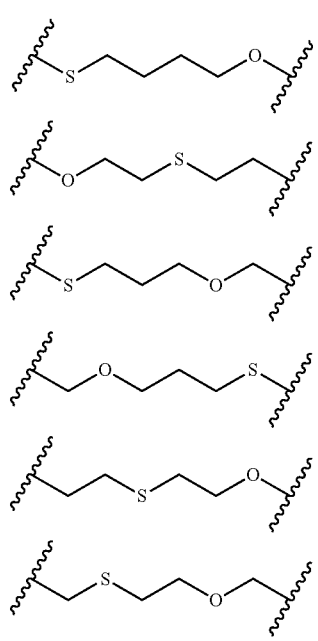

Alternatively, in certain embodiments A is —(CH$_2$)$_m$—Ar—(CH$_2$)$_o$—, wherein the sum of m and o is 1, 2, 3, or 4, and wherein 1 —CH$_2$— may be replaced by S or O, and 1 —CH$_2$—CH$_2$-may be replaced by —CH═CH— or —C≡C—.

A$^0$ is —(CH$_2$)$_m$—Ar—(CH$_2$)$_o$—, wherein the sum of m and o is 1, 2, 3, or 4, and wherein 1 —CH$_2$— may be replaced by S or O, and 1 —CH$_2$—CH$_2$— may be replaced by —CH═CH— or —C≡C—.

Ar is aryl of a formula C$_{3-10}$H$_{0-23}$N$_{0-4}$O$_{0-4}$S$_{0-4}$F$_{0-5}$Cl$_{0-3}$Br$_{0-3}$I$_{0-3}$. The formula C$_{3-10}$H$_{0-23}$N$_{0-4}$O$_{0-4}$S$_{0-4}$F$_{0-5}$Cl$_{0-3}$Br$_{0-3}$I$_{0-3}$ means that Ar consists of from 3-10 carbon atoms, 0-23 hydrogen atoms, 0-4 nitrogen atoms, 0-4 oxygen atoms, 0-4 sulfur atoms, 0-5 fluorine atoms, 0-3 chlorine atoms, 0-3 bromine atoms, and 0-3 iodine atoms.

In other words,
in one embodiment A or A$^0$ comprises:
  1) a) 1, 2, 3, or 4 —CH$_2$— moieties, or
     b) 0, 1 or 2 —CH$_2$— moieties and —CH═CH— or —C≡C—; and
  2) Ar;
e.g. —CH$_2$—Ar—, —(CH$_2$)$_2$—Ar—, —CH═CH—Ar—, —C≡C—Ar—, —CH$_2$—Ar—CH$_2$—, —CH$_2$Ar—(CH$_2$)$_2$—, —CH$_2$Ar—CH═CH—, —CH$_2$Ar—C≡C—, —(CH$_2$)$_2$—Ar—(CH$_2$)$_2$—, and the like;
in another embodiment A or A$^0$ comprises:
  1) a) O; and 0, 1, 2, or 3 —CH$_2$— moieties; or
     b) O; and 0 or 1 —CH$_2$— moieties and —CH═CH— or —C≡C—; and
  2) Ar;
e.g., —O—Ar—, —Ar—CH$_2$—O—, —O—Ar—(CH$_2$)$_2$—, —OAr—CH═CH—, —O—Ar—C≡C—, —O—CH$_2$—Ar—, —O—CH$_2$—Ar—(CH$_2$)$_2$, —O—CH$_2$Ar—CH═CH—, —O—CH$_2$Ar—C≡C—, and the like; or
in another embodiment A or A$^0$ comprises:
  1) a) S; and 0, 1, 2, or 3 —CH$_2$— moieties; or
     b) S; and 0 or 1 —CH$_2$— moieties and —CH═CH— or —C≡C—; and
  2) Ar;
e.g., —S—Ar—, —Ar—CH$_2$—S—, —S—Ar—(CH$_2$)$_2$—, —SAr—CH═CH—, —S—Ar—C≡C—, —S—CH$_2$—Ar—, —S—CH$_2$—Ar—(CH$_2$)$_2$, —S—CH$_2$Ar—CH═CH—, —S—CH$_2$Ar—C≡C—, and the like.

In another embodiment, the sum of m and o is 2, 3, or 4 wherein one CH$_2$ may be replaced with S or O and 1 —CH$_2$—CH$_2$— may be replaced by —CH═CH— or —C≡C—.

In another embodiment, the sum of m and o is 3 wherein one CH$_2$ may be replaced with S or O and 1 —CH$_2$—CH$_2$— may be replaced by —CH═CH— or —C≡C—.

In another embodiment, the sum of m and o is 2 wherein one CH$_2$ may be replaced with S or O or 1 —CH$_2$—CH$_2$— may be replaced by —CH═CH— or —C≡C—.

In another embodiment, the sum of m and o is 4 wherein one CH$_2$ may be replaced with S or O and 1 —CH$_2$—CH$_2$— may be replaced by —CH═CH— or —C≡C—.

In another embodiment, Ar is imidazolyl, pyrrolyl, furanyl, oxazolyl, thiazolyl, thienyl, pyridinyl, or phenyl with 1 or 2 substituents selected from: C$_{1-3}$ alkyl, —OH, —SH, C$_{1-3}$ —O-alkyl, C$_{1-3}$ —S-alkyl, —F, —Cl, —Br, or —CF$_3$.

In another embodiment, Ar is thienyl.

In other embodiments, A or A$^0$ has one of the following structures, wherein Y attaches to the ring.

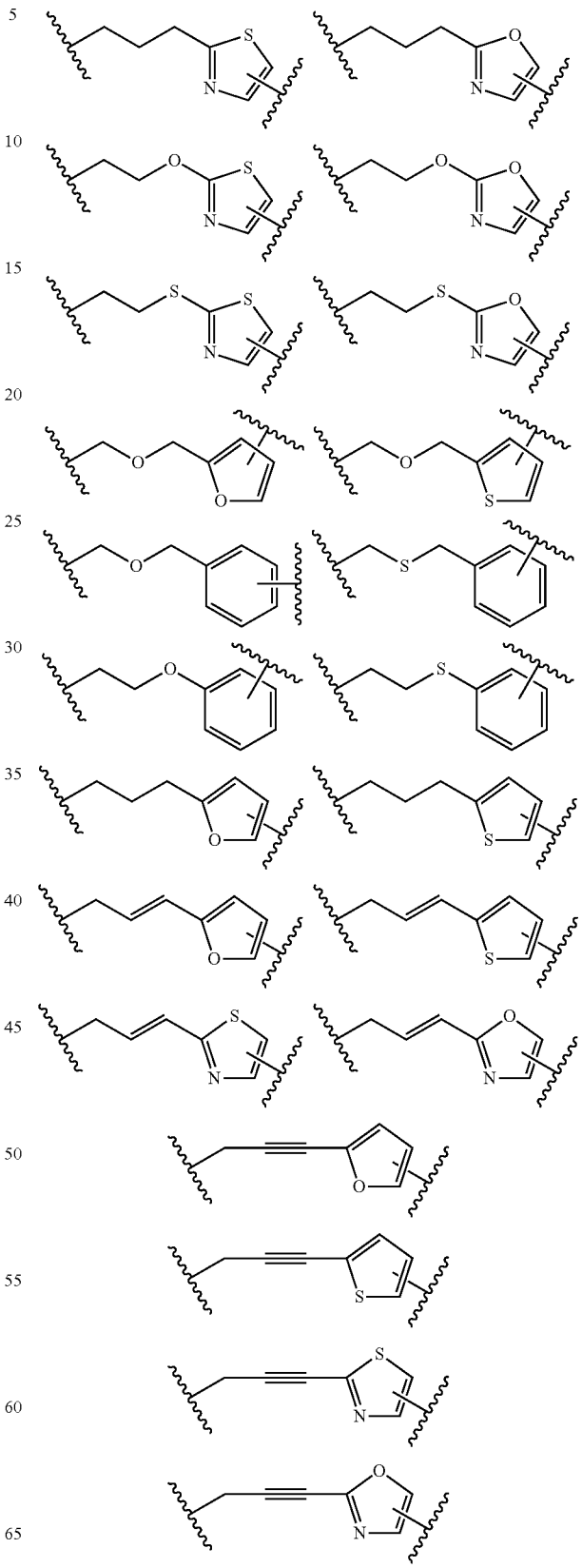

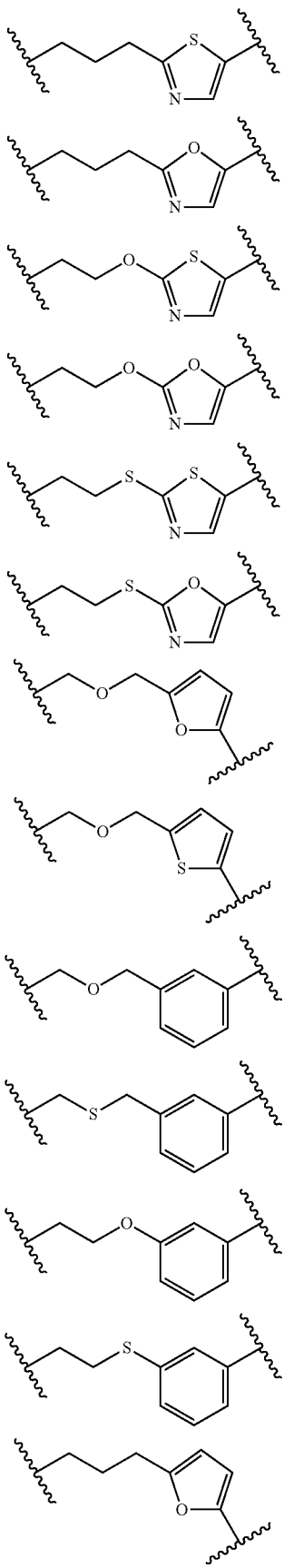
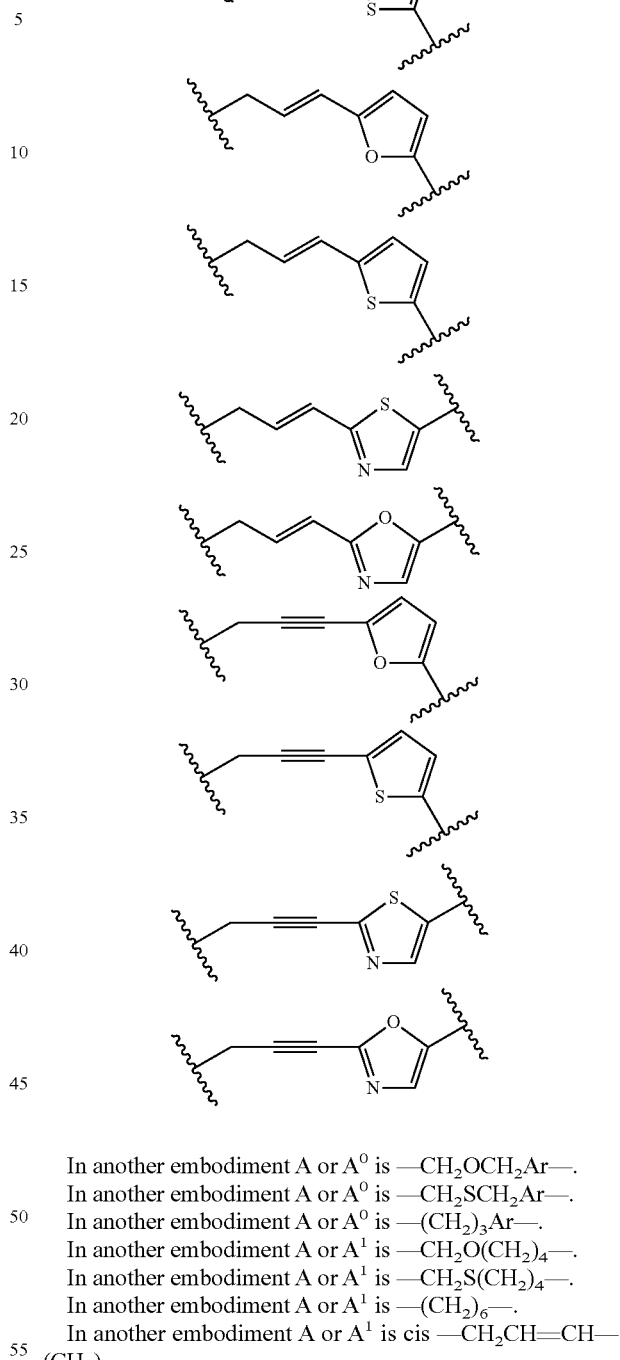

In another embodiment A or A⁰ is —CH₂OCH₂Ar—.
In another embodiment A or A⁰ is —CH₂SCH₂Ar—.
In another embodiment A or A⁰ is —(CH₂)₃Ar—.
In another embodiment A or A¹ is —CH₂O(CH₂)₄—.
In another embodiment A or A¹ is —CH₂S(CH₂)₄—.
In another embodiment A or A¹ is —(CH₂)₆—.
In another embodiment A or A¹ is cis —CH₂CH═CH—(CH₂)₃—.
In another embodiment A or A¹ is —CH₂C≡C—(CH₂)₃—.
In another embodiment A or A¹ is —S(CH₂)₃S(CH₂)₂—.
In another embodiment A or A¹ is —(CH₂)₄OCH₂—.
In another embodiment A or A¹ is cis —CH₂CH═CH—CH₂OCH₂—.
In another embodiment A or A¹ is —CH₂CH═CH—CH₂OCH₂—.
In another embodiment A or A¹ is —(CH₂)₂S(CH₂)₃—.
In another embodiment A or A¹ is —CH₂—O—(CH₂)₄—.
In another embodiment A or A¹ is 6-hexyl.

In another embodiment A or $A^1$ is (Z)-6-hex-4-enyl.
G is —H, —OH, =O, —F, —CN.
In one embodiment, G is —H, such as in the examples below.
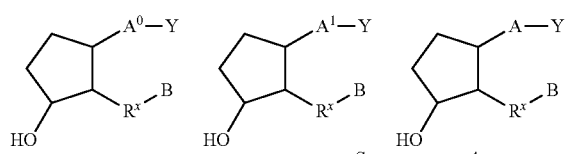
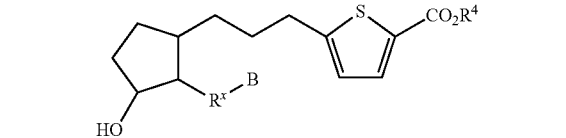
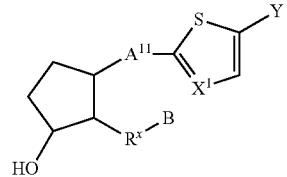
In one embodiment, G is —OH, such as in the examples below.
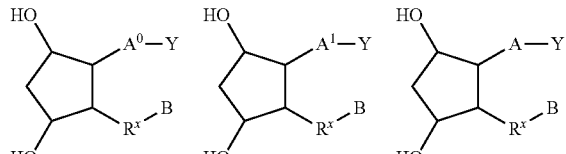
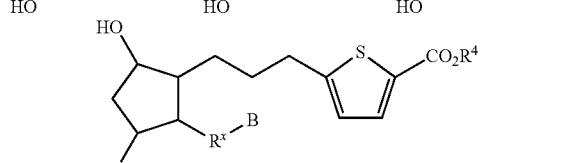
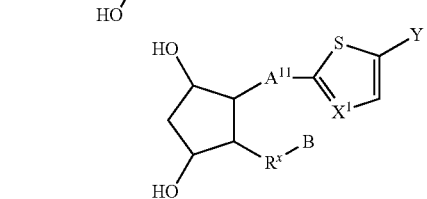
In one embodiment, G is =O, such as in the examples below.
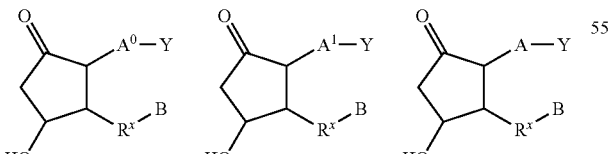
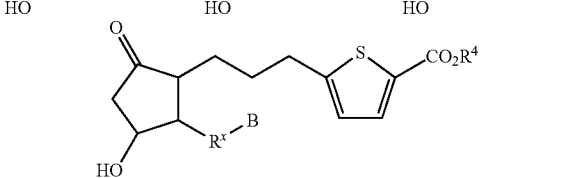
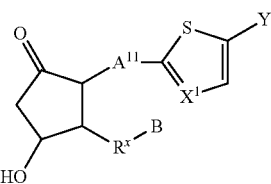
In one embodiment, G is —Cl, such as in the examples below.
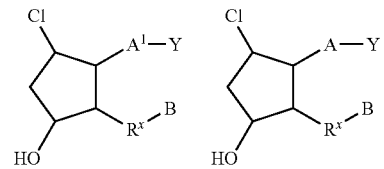
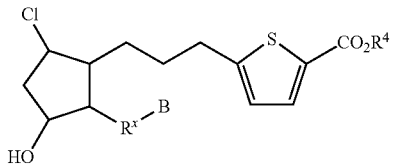
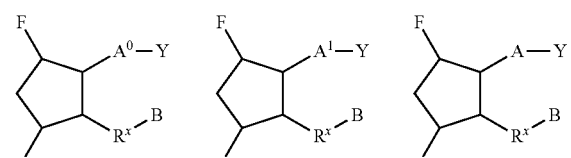
In one embodiment, G is —F, such as in the examples below.
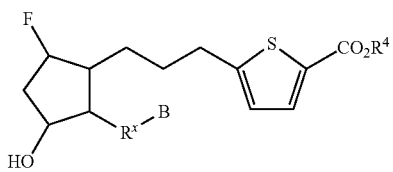
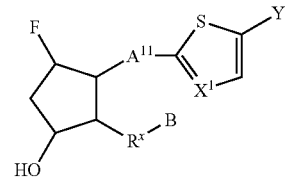

In one embodiment, G is —CN, such as in the examples below.

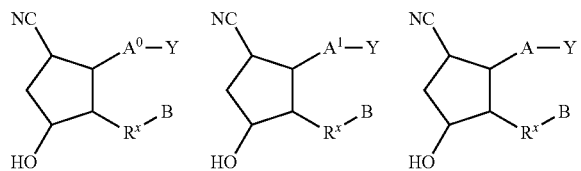

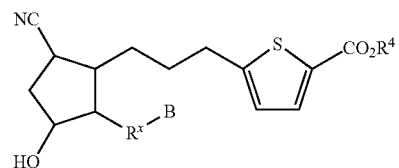

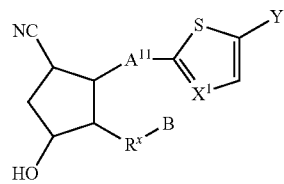

In another embodiment, G is —F, —Cl, or =O.
$R^x$ is —(CH$_2$)$_3$—, —CH=CHCH$_2$—, —CH=C=CH—, —CH$_2$OCH$_2$—, —CH$_2$SCH$_2$—, —CH$_2$NHCH$_2$—, —(CH$_2$)$_2$O—, —(CH$_2$)$_2$S—, or —(CH$_2$)$_2$NH—.

In one embodiment, $R^x$ is —(CH$_2$)$_3$—, such as in the examples below.

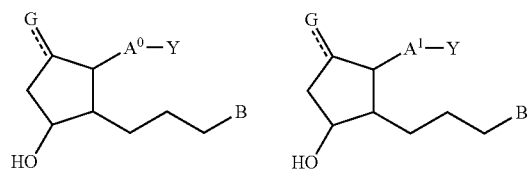

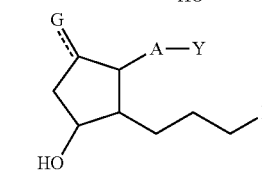

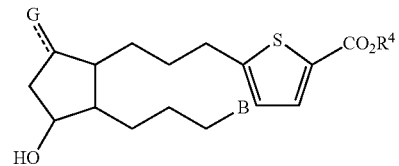

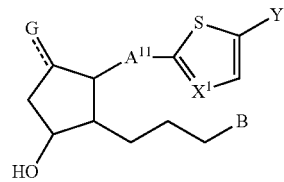

In one embodiment, $R^x$ is —CH=CHCH$_2$—, such as in the examples below.

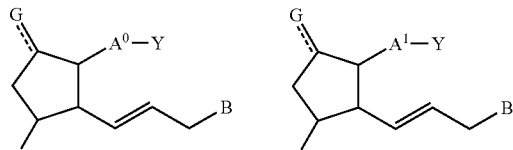

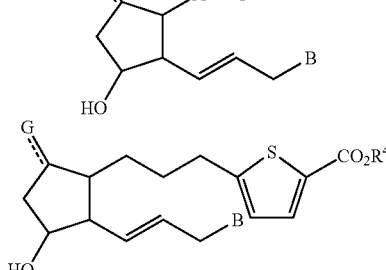

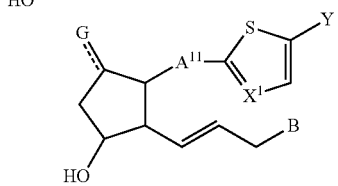

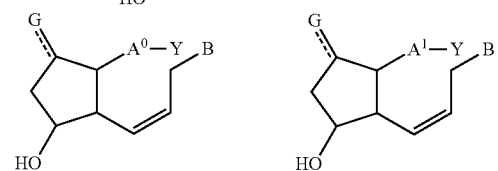

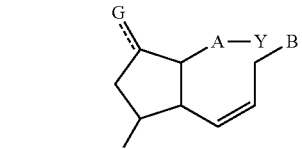

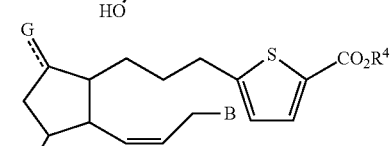

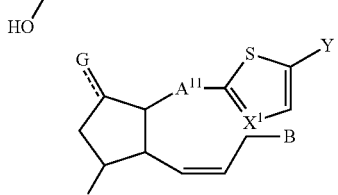

In one embodiment, $R^x$ is —CH=C=CH—, such as in the examples below.

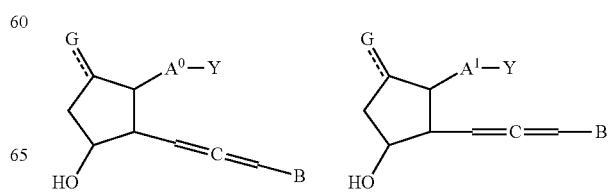

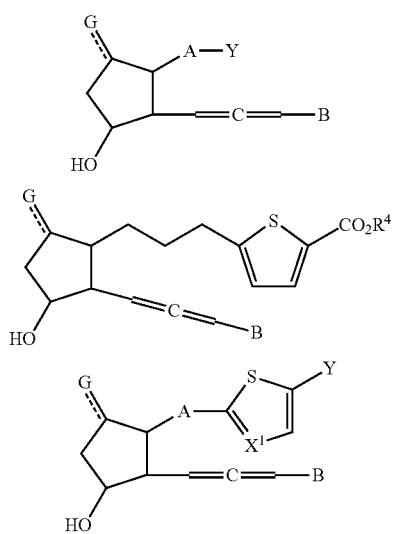
In one embodiment, $R^x$ is —CH$_2$OCH$_2$—, such as in the examples below.
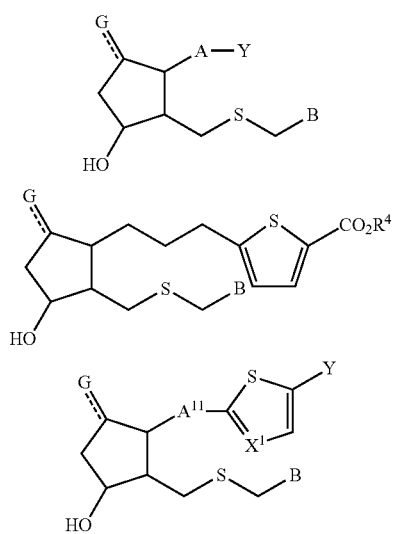
In one embodiment, $R^x$ is —CH$_2$NHCH$_2$—, such as in the examples below.
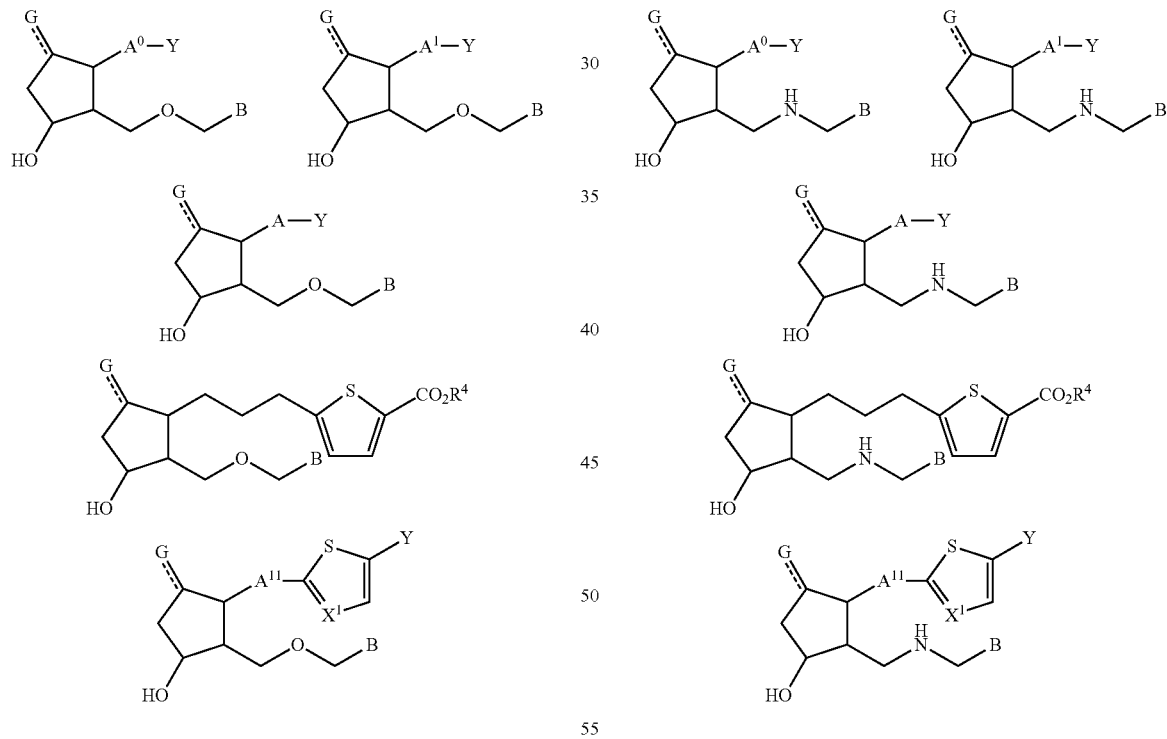
In one embodiment, $R^x$ is —CH$_2$SCH$_2$—, such as in the examples below.
In one embodiment, $R^x$ is —(CH$_2$)$_2$O—, such as in the examples below.
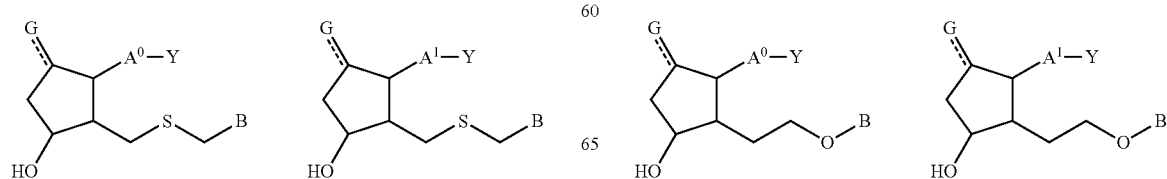

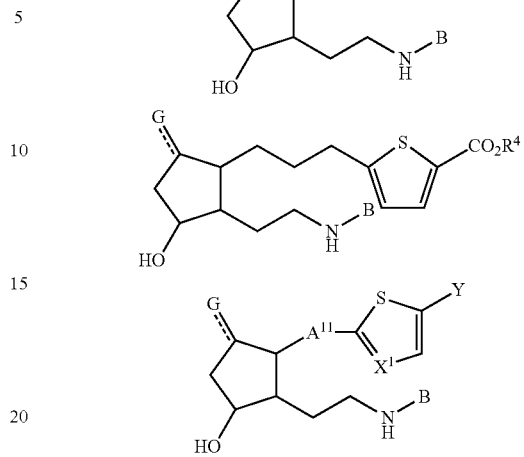

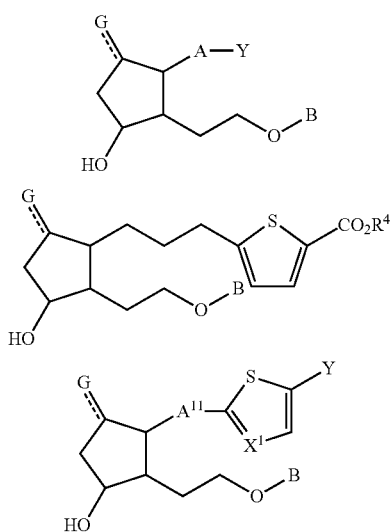

In one embodiment, $R^x$ is —$(CH_2)_2S$—, such as in the examples below.

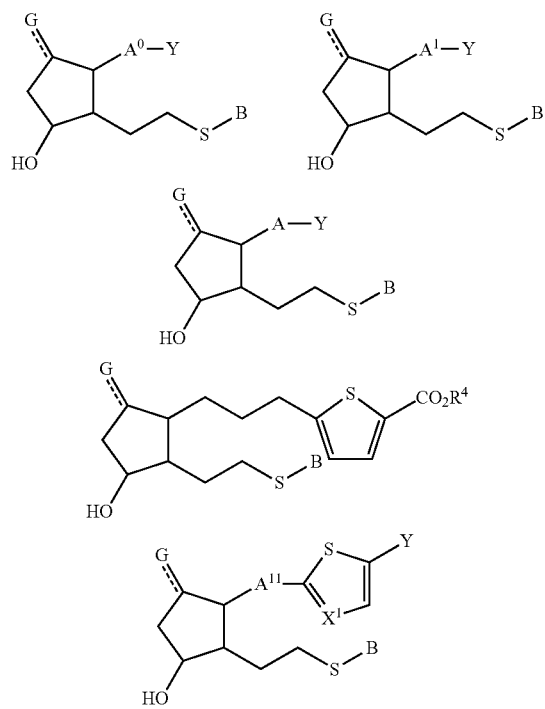

In one embodiment, $R^x$ is —$(CH_2)_2NH$—, such as in the examples below.

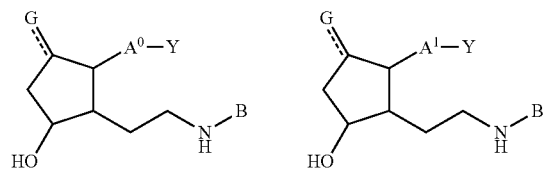

In another embodiment, $R^x$ is —$(CH_2)_3$—, —CH=CHCH$_2$—, —CH=C=CH—, —CH$_2$OCH$_2$—, CH$_2$SCH$_2$—, or —CH$_2$NHCH$_2$—.

B is aryl of a formula $C_{3-20}H_{0-45}N_{0-4}O_{0-4}S_{0-4}F_{0-5}Cl_{0-3}Br_{0-3}I_{0-3}$. The formula $C_{3-20}H_{0-45}N_{0-4}O_{0-4}S_{0-4}F_{0-5}Cl_{0-3}Br_{0-3}I_{0-3}$ means that B consists of from 3-20 carbon atoms, 0-45 hydrogen atoms, 0-4 nitrogen atoms, 0-4 oxygen atoms, 0-4 sulfur atoms, 0-5 fluorine atoms, 0-3 chlorine atoms, 0-3 bromine atoms, and 0-3 iodine atoms.

In one embodiment, B is imidazolyl, pyrrolyl, furanyl, oxazolyl, thiazolyl, thienyl, pyridinyl, or phenyl with 1 or 2 substituents selected from: $C_{1-10}$ alkyl, —OH, —SH, $C_{1-10}$ —O-alkyl, $C_{1-10}$ —S-alkyl, $C_{1-10}$ hydroxyalkyl, $C_{1-10}$ acyl, —F, —Cl, —Br, I, or —CF$_3$.

In one embodiment B is phenyl with from 1 to 4 substituents independently selected from: hydrocarbyl, alkyl, acyl, ether substituents, —O-alkyl, thioether substituents, —S-alkyl, amine substituents, aminoalkyl, ester substituents, hydroxyalkyl, fluorocarbons, —CF$_3$, —CN, —F, —Cl, —Br, and —I.

In one embodiment, B is phenyl substituted with from 1 to 4 substituents selected from: $C_{2-8}$ alkyl, $C_{1-8}$ —O-alkyl, $C_{1-8}$ hydroxyalkyl, —OH, —F, —Cl, —Br, or —CF$_3$.

In one embodiment B is pyridinyl with from 1 to 3 substituents independently selected from: hydrocarbyl, alkyl, acyl, ether substituents, —O-alkyl, thioether substituents, —S-alkyl, amine substituents, aminoalkyl, ester substituents, hydroxyalkyl, fluorocarbons, —CF$_3$, —CN, —F, —Cl, —Br, and —I.

In one embodiment B is thienyl with from 1 to 2 substituents independently selected from: hydrocarbyl, alkyl, acyl, ether substituents, —O-alkyl, thioether substituents, —S-alkyl, amine substituents, aminoalkyl, ester substituents, hydroxyalkyl, fluorocarbons, —CF$_3$, —CN, —F, —Cl, —Br, and —I.

In one embodiment B is furyl with from 1 to 2 substituents independently selected from: hydrocarbyl, alkyl, acyl, ether substituents, —O-alkyl, thioether substituents, —S-alkyl, amine substituents, aminoalkyl, ester substituents, hydroxyalkyl, fluorocarbons, —CF$_3$, —CN, —F, —Cl, —Br, and —I.

In one embodiment, the compound is not:
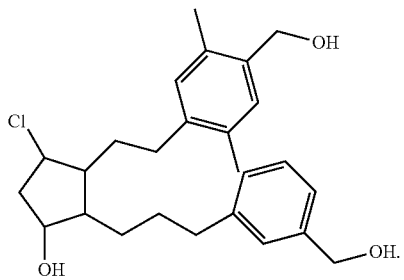 [SMILES: Cc1cc(CCC2C(Cl)CC(O)C2CCCc2cccc(CO)c2)c(C)cc1CO]
Another embodiment is a compound represented by a formula:
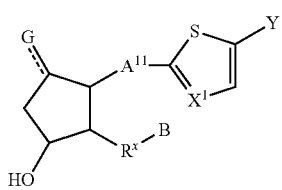
wherein $A^{11}$ is —(CH$_2$)$_3$—, —O(CH$_2$)$_2$—, —CH$_2$OCH$_2$—, —(CH$_2$)$_2$O—, —S(CH$_2$)$_2$—, —CH$_2$SCH$_2$—, or —(CH$_2$)$_2$S—, and $X^1$ is N or CH.
Another embodiment is a compound represented by a formula:
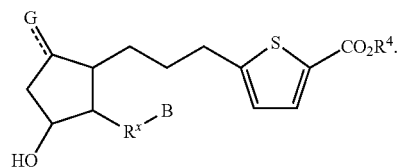
Another embodiment is a compound selected from:
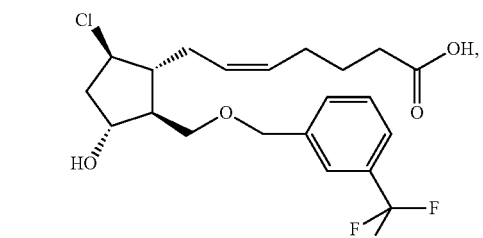
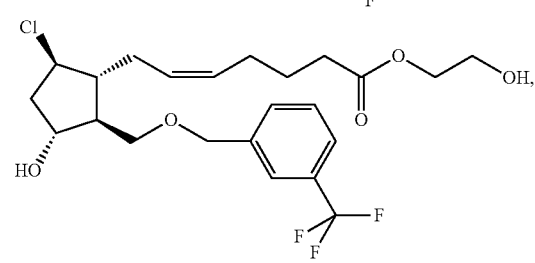
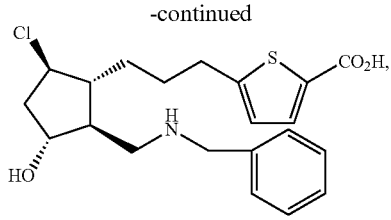
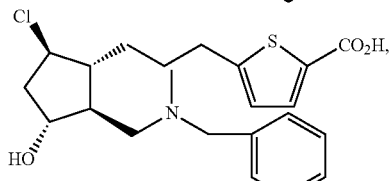
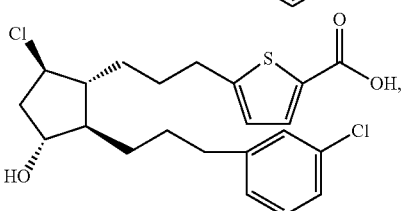
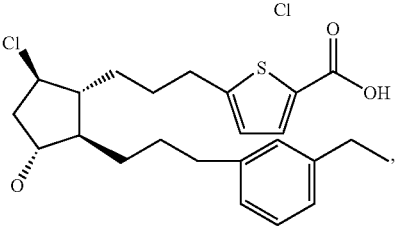
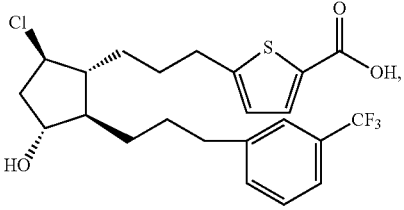
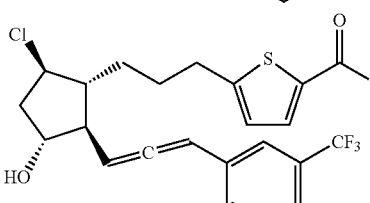
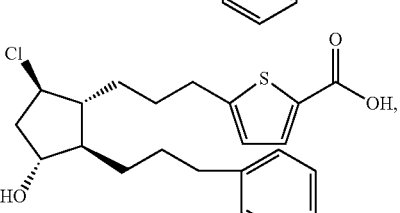
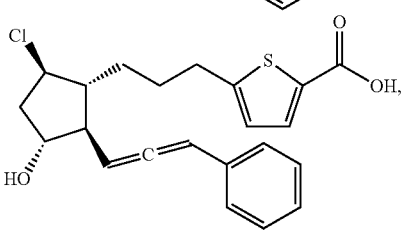

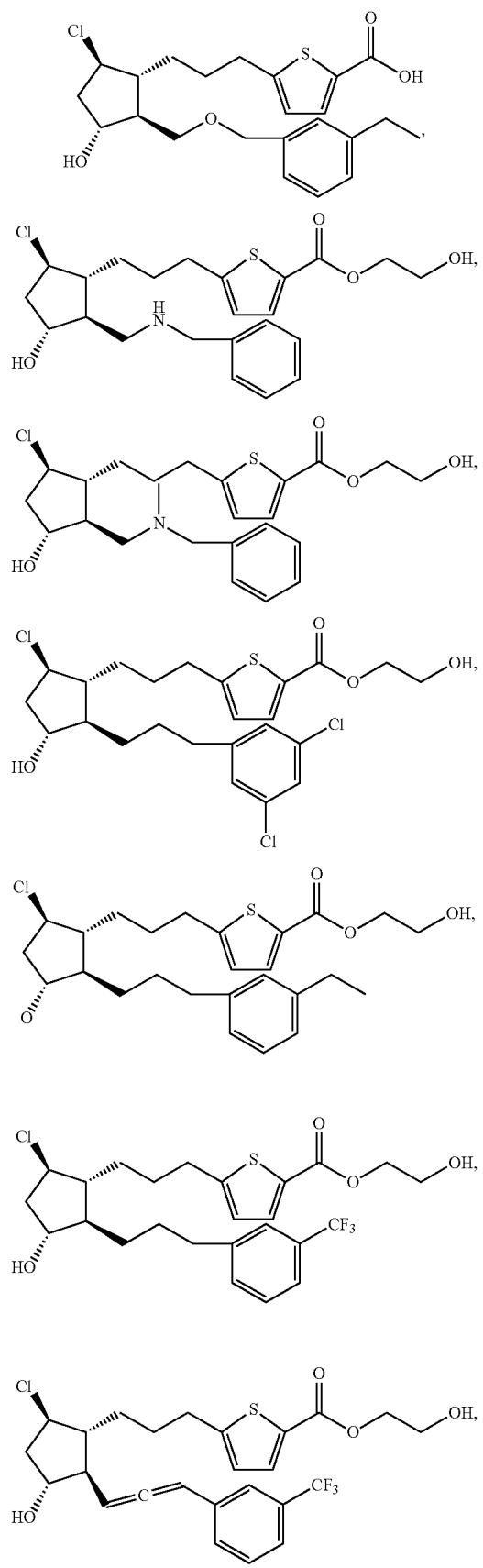
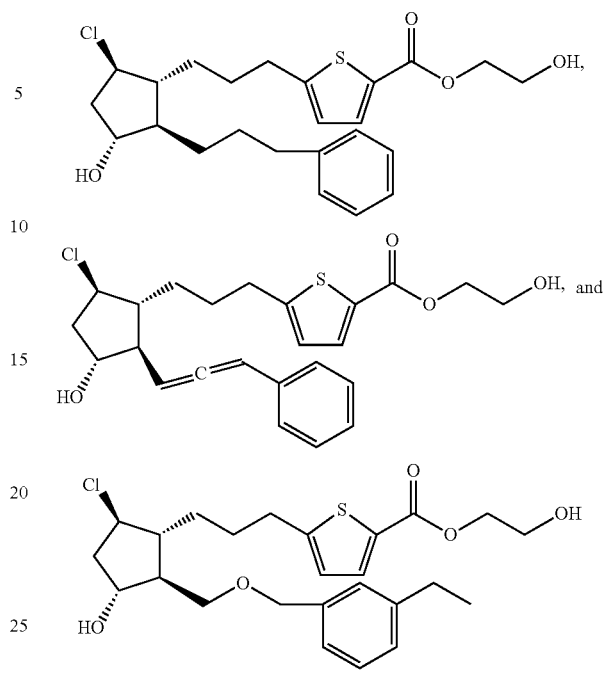
In another embodiment, the compound is not:
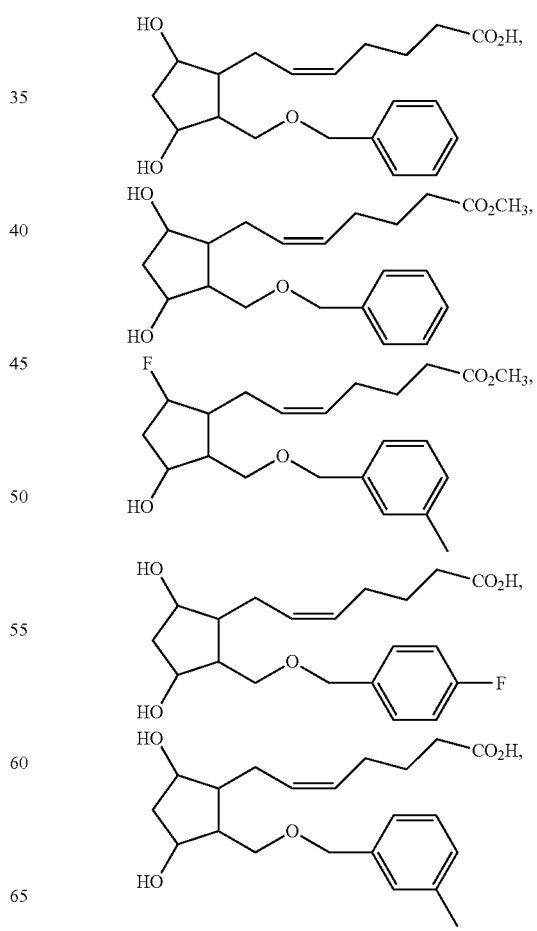

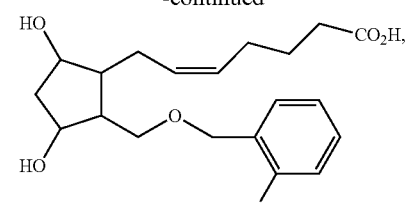

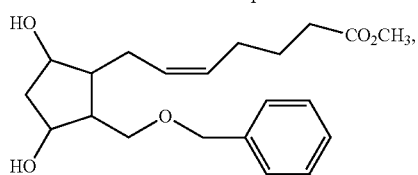

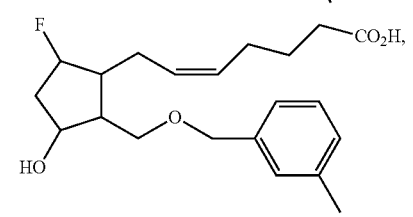

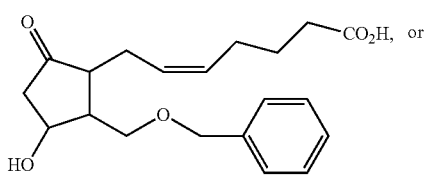

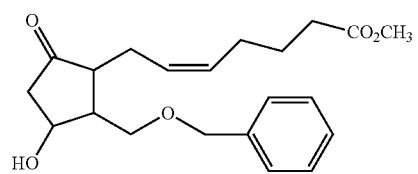

Another embodiment is a method of: reducing intraocular pressure, treating glaucoma or intraocular pressure, growing hair, or improving the appearance of hair, comprising administering a compound disclosed herein to a mammal in need thereof.

Another embodiment is use of a compound disclosed herein in the manufacture of a medicament for: reducing intraocular pressure, treating glaucoma or intraocular pressure, growing hair, or improving the appearance of hair.

Some hypothetical examples of useful compounds are shown below.

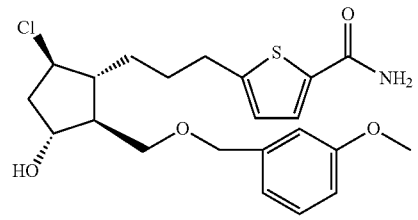

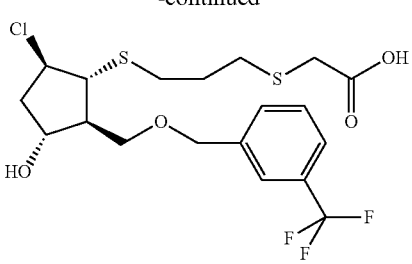

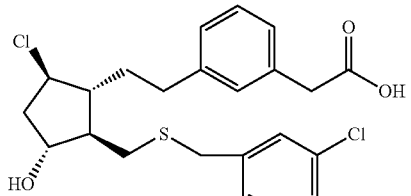

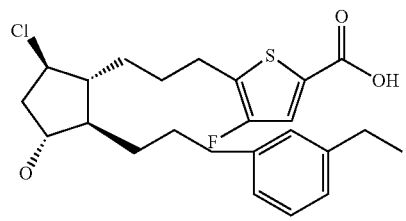

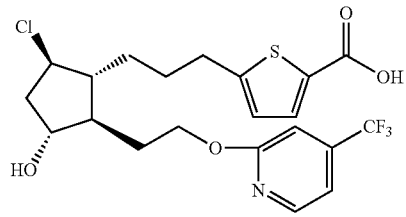

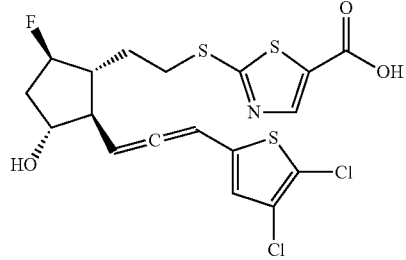

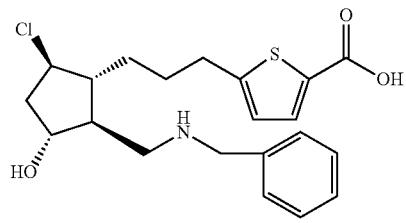

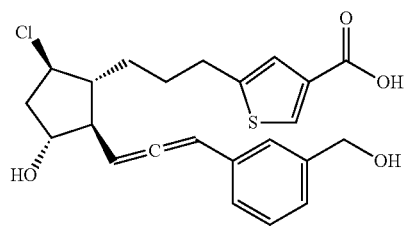

29
-continued
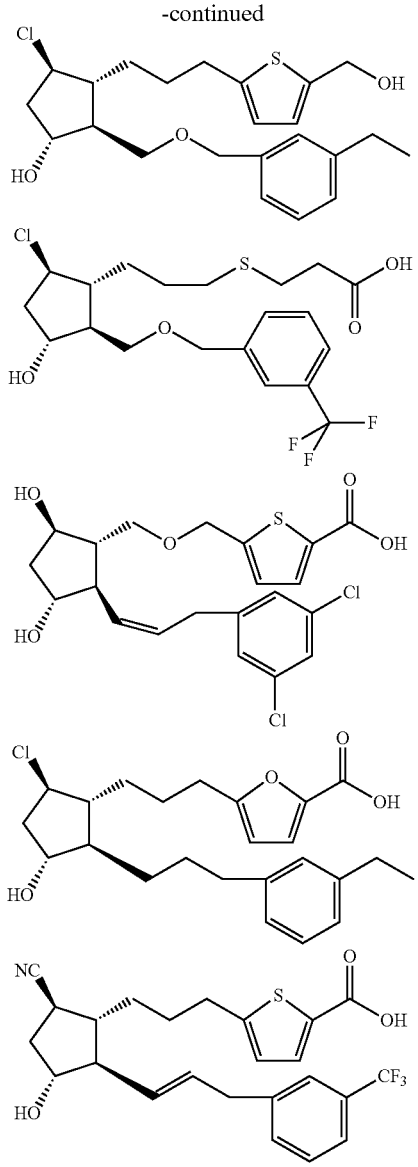
30
-continued
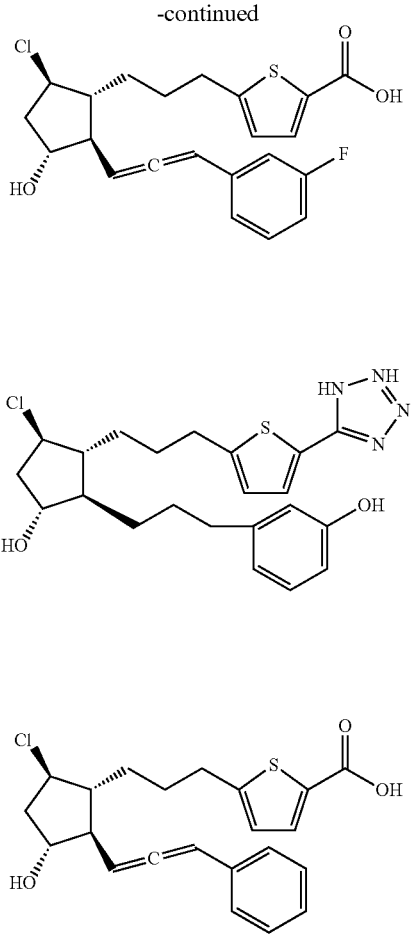
SYNTHETIC EXAMPLES
Although the compound disclose herein may be prepared by any of a number of potential methods, the methods are below are examples of useful methods that may be used.
Scheme 1
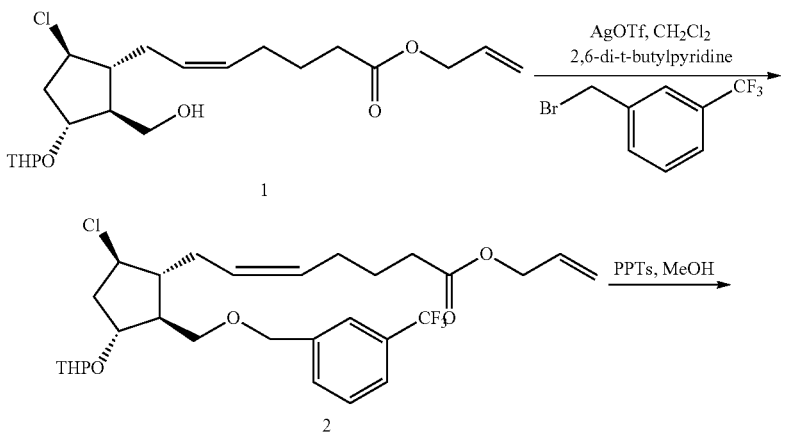

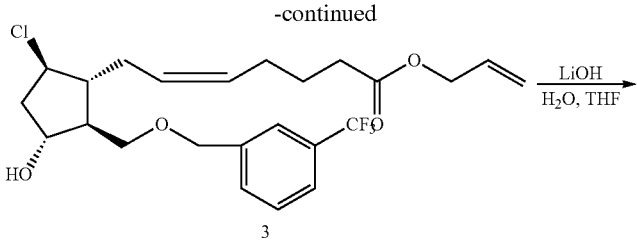

3

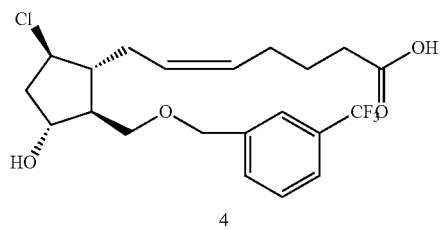

4

Example 1

(Z)-7-((1R,2S,3R,5R)-5-chloro-3-hydroxy-2-((3-(trifluoromethyl)benzyloxy)methyl)cyclopentyl) hept-5-enoic acid (4)

Step 1: Alkylation of 1 to Give 2

A solution of (Z)-7-[(1R,2S,3R,5R)-5-chloro-2-hydroxymethyl-3-(tetrahydropyran-2-yloxy)-cyclopentyl]-hept-5-enoic acid allyl ester (1, see WO2006/076370, 146 mg, 0.36 mmol), silver triflate (103 mg, 0.40 mmol) and 2,6-di-t-butylpyridine (122 μL, 0.54 mmol) in $CH_2Cl_2$ (1.0 mL) was cooled to 0° C. 3-(Trifluoromethyl)benzyl bromide (67 μL, 0.44 mmol) was added and a slight precipitate formed. After several hours the reaction was filtered through celite and the filtrate was washed with 1 N HCl, saturated aqueous $NaHCO_3$ and brine then dried ($MgSO_4$), filtered and concentrated in vacuo. Purification of the crude residue by flash column chromatography on silica gel (20% EtOAc/hexanes) afforded 41 mg (20%) of 2.

Step 2: Deprotection of 2 to Give 3

Pyridinium p-toluenesulfonate (PPTs, 5 mg, 0.020 mmol) was added to a solution of 2 (41 mg, 0.073 mmol) in methanol (2.0 mL) at room temperature. The solution stirred at room temperature for 16 h then concentrated in vacuo. Purification of the crude residue by flash column chromatography on silica gel (30% EtOAc/hexane) afforded 27 mg (78%) of 3.

Step 3. Saponification of 3 to Give 4

Lithium hydroxide (0.2 mL of a 1.0 M aqueous solution, 0.2 mmol) was added to a solution of 3 (27 mg, 0.057 mmol) in THF (1.0 mL). After stirring overnight at room temperature, 10% citric acid and brine were added and the mixture was extracted with EtOAc (3×20 mL). The combined extracts were dried ($MgSO_4$), filtered and concentrated in vacuo. Purification of the crude residue by flash column chromatography on silica gel (8% MeOH/$CH_2Cl_2$) afforded 15 mg (61%) of the title compound (4).

Scheme 2

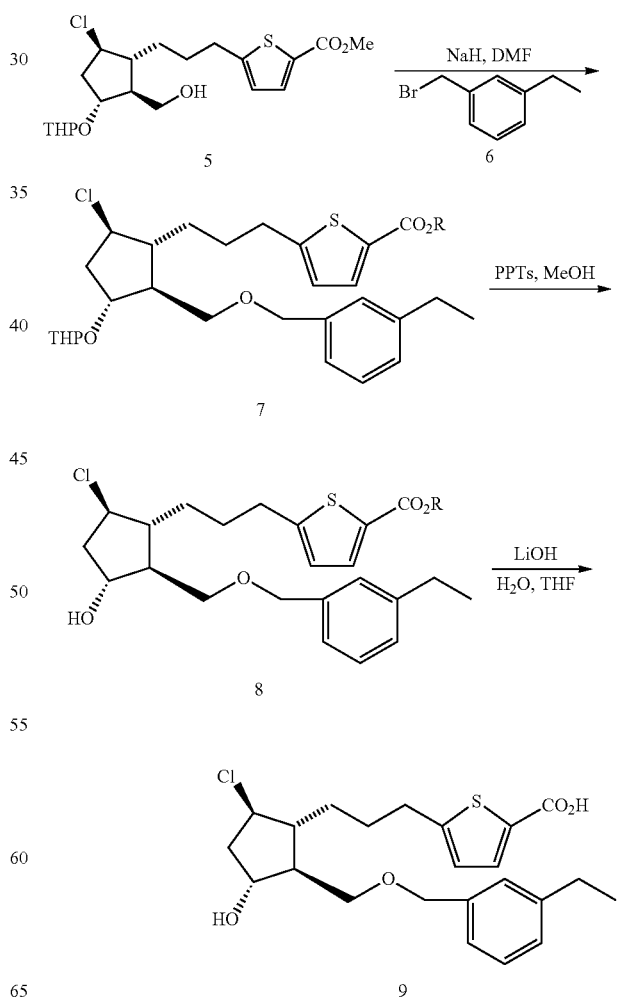

Example 2

5-(3-(((1R,2S,3R,5R)-5-chloro-2-((3-ethylbenzyloxy) methyl)-3-hydroxycyclopentyl)propyl)thiophene-2-carboxylic acid (9)

Step 1: Alkylation of 5 with 6 to Give 7

Sodium hydride (60% dispersion in mineral oil, 14.4 mg, 0.36 mmol) was added to a solution of methyl 5-(3-((1R,2S, 3R,5R)-5-chloro-2-(hydroxymethyl)-3-(tetrahydro-2H-pyran-2-yloxy)cyclopentyl)propyl)thiophene-2-carboxylate (5, see US 2007/0293561, 100 mg, 0.24 mmol) in DMF (0.6 mL) at 0° C., and the reaction was allowed to warm to room temperature. After 30 min, the reaction was cooled to −40° C. and a solution of 1-(bromomethyl)-3-ethylbenzene (preparation 1, 60 mg, 0.30 mmol) in DMF (0.6 mL) was added via cannula. After 45 min at −40° C., the reaction was allowed to warm to room temperature. After 18 h, the reaction was quenched by the addition of saturated aqueous $NH_4Cl$, diluted with water (5 mL) and extracted with EtOAc (40 mL). The organic phase was washed with water (2×15 mL) and brine (15 mL) then dried ($Na_2SO_4$), filtered and concentrated in vacuo. Purification of the crude residue by chromatography on silica gel (hexanes→50% EtOAc/hexanes, gradient) afforded 26 mg (~18%) of an inseparable mixture of methyl and 3-ethylbenzyl esters 7.

Step 2: Deprotection of 7 to Give 8

PPTs (2 mg, 0.008 mmol) was added to a solution of 7 (26 mg, ~0.04 mmol) in methanol (0.43 mL) at room temperature. The solution stirred 40° C. for 18 h, then cooled and concentrated in vacuo. Purification of the crude residue by flash column chromatography on silica gel (hexanes→50% EtOAc/hexanes, gradient) afforded 24 mg (quant.) of an inseparable mixture of methyl and 3-ethylbenzyl esters 8 (approximately 3:2 in favor of the 3-ethylbenzyl ester).

Step 3. Saponification of 8 to Give 9

Lithium hydroxide (0.2 mL of a 1.0 M aqueous solution, 0.2 mmol) was added to a solution of 8 (24 mg, ~0.04 mmol) in THF (0.4 mL). The mixture was heated at 40° C. for 4 days then cooled to room temperature. Water (2 mL) was added and the mixture was acidified with 1 N HCl (1 mL) and extracted with EtOAc (3×10 mL). The combined organic phase was dried ($Na_2SO_4$), filtered and concentrated in vacuo. Purification of the crude residue by chromatography on silica gel ($CH_2Cl_2$→10% MeOH/$CH_2Cl_2$, gradient) afforded 13.5 mg (75%) of the title compound (9).

Step 2. Reduction of methyl 3-ethylbenzoate to Form (3-ethylphenyl)methanol
Step 3. Bromination of (3-ethylphenyl)methanol to Form 1-(bromomethyl)-3-ethylbenzene

Preparation 1

1-(bromomethyl)-3-ethylbenzene (for an Alternative Synthesis, see Kindon et al.: WO98/54180)

Step 1. Alkylation of 3-ethylbenzoic Acid to Form methyl 3-ethylbenzoate

Concentrated $H_2SO_4$ (1.0 mL) was added to a solution of 3-ethylbenzoic acid (500 mg, 3.33 mmol) in MeOH (10 mL). The mixture was heated at reflux for 18 h then cooled to room temperature. The mixture was diluted with water (50 mL) and extracted with $Et_2O$ (3×100 mL). The combined organic phase was dried ($Na_2SO_4$), filtered and concentrated in vacuo. Purification of the crude residue by chromatography on silica gel (hexanes→20% EtOAc/hexanes, gradient) afforded 500 mg (91%) of methyl 3-ethylbenzoate.

Step 2. Reduction of methyl 3-ethylbenzoate to Form (3-ethylphenyl)methanol

Lithium aluminum hydride (3.1 mL of 1.0 M solution in THF, 3.1 mmol) was added to a solution of methyl 3-ethylbenzoate (500 mg, 3.05 mmol) in THF (12 mL) at 0° C. After 2 h at 0° C., the reaction was quenched by the addition of saturated aqueous Rochelle's salt (50 mL) and stirred vigorously overnight at room temperature. The reaction mixture was extracted with $Et_2O$ (3×100 mL). The combined organic phase was dried ($Na_2SO_4$), filtered and concentrated in vacuo to afford (3-ethylphenyl)methanol which was shown to be ~90% pure by $^1H$ NMR analysis and was taken on without further purification.

Step 3. Bromination of (3-ethylphenyl)methanol to Form 1-(bromomethyl)-3-ethylbenzene Bromine (0.21 mL, 4.08 mmol) was added dropwise to a solution of triphenylphosphine (1.08 g, 4.12 mmol) and imidazole (280 mg, 4.11 mmol) in $CH_2Cl_2$ (13.5 mL) at 0° C. The mixture was allowed to warm to room temperature and then a solution of (3-ethylphenyl)methanol (~3.05 mmol) in $CH_2Cl_2$ (3.5 mL) was added. After 1 h, the mixture was diluted with hexanes and filtered through celite, washing with excess hexanes. The filtrate was concentrated in vacuo. Purification of the crude residue by chromatography on silica gel (hexanes→10% EtOAc/hexanes, gradient) afforded 530 mg (87% over two steps) of 1-(bromomethyl)-3-ethylbenzene.

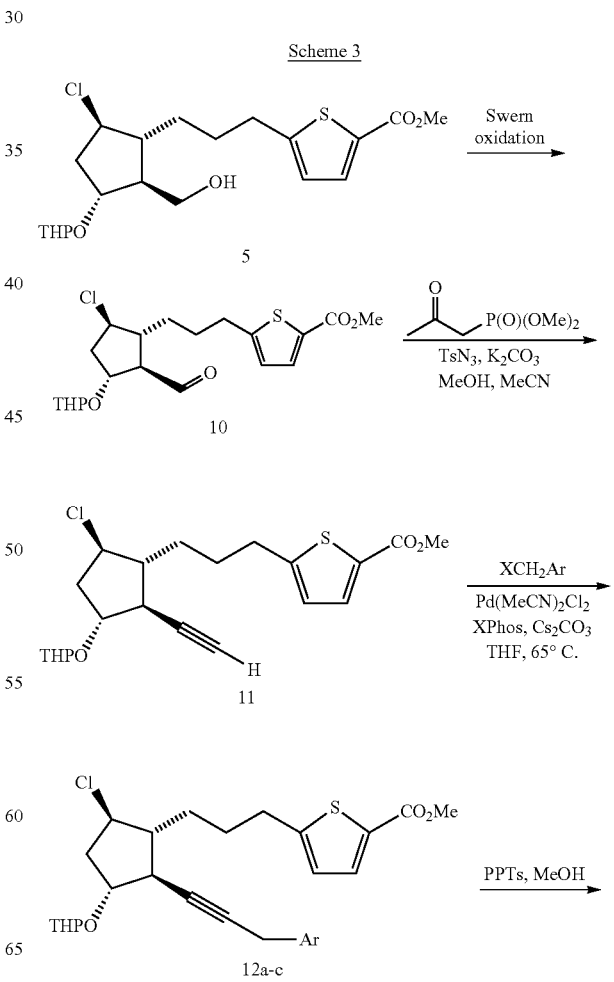

Scheme 3

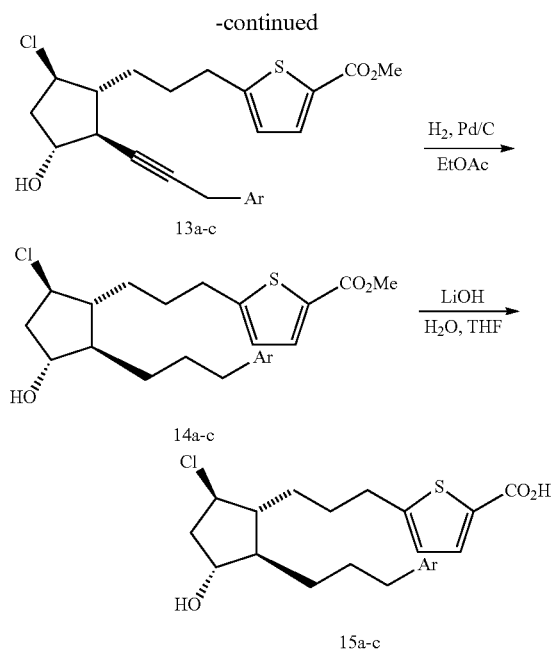

Example 3

5-(3-((1R,2S,3R,5R)-5-chloro-2-(3-(3,5-dichlorophenyl)propyl)-3-hydroxycyclopentyl)propyl)thiophene-2-carboxylic acid (15a)

Step 1. Reaction of 11 with 3,5-dichlorobenzyl Chloride to Give 12a in Accordance with the Procedures of Larson, Anderson, Tundel and Buchwald: *Synlett* 2006, 2941-2946.

Cesium carbonate (53 mg, 0.16 mmol), bis(acetonitrile)palladium (II) chloride (2.7 mg, 0.010 mmol) and 2-dicyclohexylphosphino-2',4',6'-triisopropylbiphenyl (XPhos, 12.2 mg, 0.026 mmol) were combined in a 1 dram vial. The mixture was purged with nitrogen then 3,5-dichlorobenzyl chloride (30 mg, 0.15 mmol) and a solution of alkyne 11 (see preparation 2, 70 mg, 0.17 mmol) in THF (0.3 mL) were added sequentially. The vial was sealed under nitrogen and heated at 65° C. overnight. The mixture was then cooled, diluted with EtOAc and filtered through celite. The filtrate was concentrated in vacuo. Purification of the crude residue by flash column chromatography on 4 g silica gel (hexanes→EtOAc, gradient) afforded 79 mg (90%) of 12a.

Step 2. Deprotection of 12a to Give 13a

PPTs (22 mg, 0.09 mmol) was added to a solution of 12a (79 mg, 0.14 mmol) in methanol (4 mL) at room temperature. The solution was stirred 40° C. for 18 h, then cooled and concentrated in vacuo. Purification of the crude residue two times by flash column chromatography on 4 g silica gel (hexanes→EtOAc, gradient) afforded 20 mg (30%) of 13a.

Step 3. Hydrogenation of 13a to Give 14a

Palladium on carbon (10 wt. %, 2 mg) was added to a solution of alkyne 13a (10 mg, 0.021 mmol) in EtOAc (0.7 mL). A hydrogen atmosphere was established by evacuating and refilling with hydrogen (3×) and the reaction mixture was stirred under a balloon of hydrogen. After 18 h, the reaction mixture was filtered through celite, washing with EtOAc, and the filtrate was concentrated in vacuo to afford 10 mg (99%) of saturated compound 14a.

Step 4. Saponification of 14a to Give 15a

Lithium hydroxide (0.2 mL of a 1.0 M aqueous solution, 0.2 mmol) was added to a solution of 14a (10 mg, 0.02 mmol) in THF (0.2 mL). After stirring 3 days at room temperature, the mixture was acidified with 1 N HCl (0.2 mL) concentrated in vacuo. The crude residue was absorbed onto silica and purified by chromatography on 4 g silica gel ($CH_2Cl_2$→20% MeOH/$CH_2Cl_2$, gradient) to afford 3 mg (31%) of the title compound (15a).

Example 4

5-(3-((1R,2R,3R,5R)-5-chloro-2-(3-(3-ethylphenyl)propyl)-3-hydroxycyclopentyl)propyl)thiophene-2-carboxylic acid (15b)

Step 1. Reaction of 11 with 3-ethylbenzyl bromide to Give 12b

In accordance with the procedure of example 3, step 1, alkyne 11 (100 mg, 0.24 mmol) and 3-ethylbenzyl bromide (33 mg, 0.17 mmol) were converted into 86 mg (87%) of 12b.

Step 2. Deprotection of 12b to Give 13b

In accordance with the procedures of example 3, step 2, THP ether 12b (86 mg, 0.16 mmol) was converted to 44 mg (61%) of 13b.

Step 3. Hydrogenation of 13b to Give 14b

In accordance with the procedures of example 3, step 3, 13b (22 mg, 0.05 mmol) was converted to 4 mg (18%) of saturated compound 14b after purification by preparative thin layer chromatography.

Step 4. Saponification of 14b to Give 15b

Lithium hydroxide (0.1 mL of a 1.0 M aqueous solution, 0.1 mmol) was added to a solution of 14b (4 mg, 0.009 mmol) in THF (0.1 mL). After stirring 2 days at room temperature, the mixture was acidified with 1 N HCl (0.2 mL) and extracted with $CH_2Cl_2$ (20 mL). The organic phase was washed with brine (1 mL) then dried ($MgSO_4$), filtered and concentrated in vacuo. Purification of the crude residue two times by flash column chromatography on 4 g silica gel ($CH_2Cl_2$→20% MeOH/$CH_2Cl_2$, gradient) afforded 2 mg (52%) of the title compound (15b).

Scheme 4

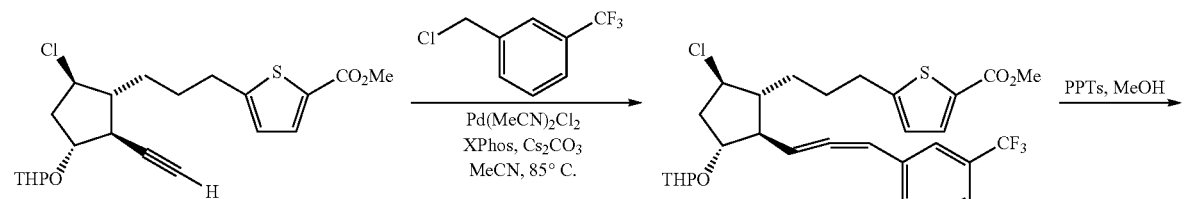

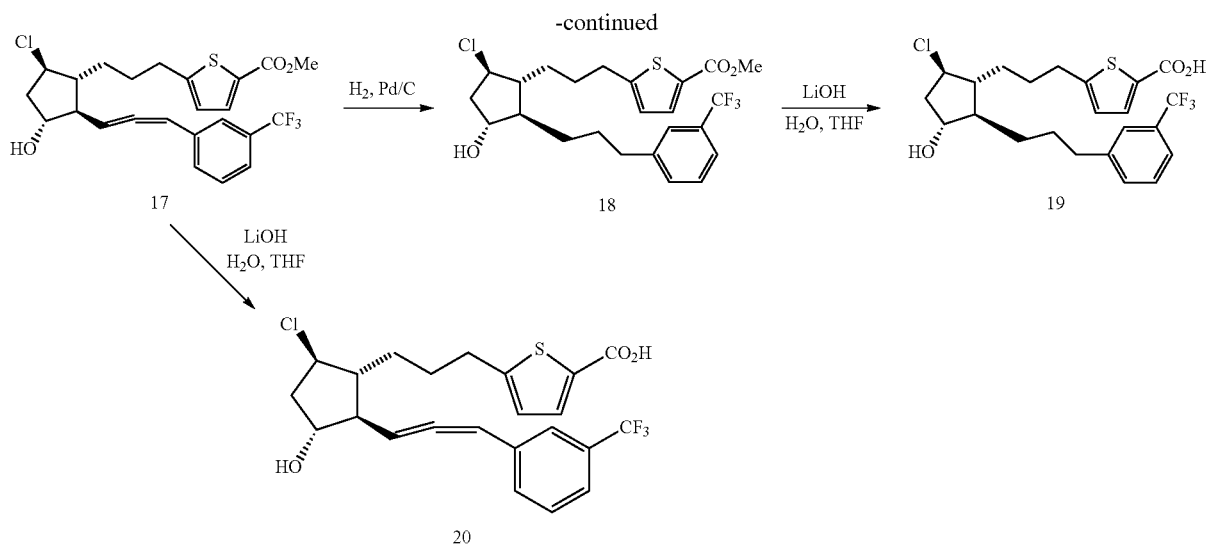

Example 5

5-(3-((1R,2R,3R,5R)-5-chloro-3-hydroxy-2-(3-(3-(trifluoromethyl)phenyl)propyl)cyclopentyl)propyl)thiophene-2-carboxylic acid (19)

Step 1. Reaction of 11 with 3-trifluoromethylbenzyl bromide to Give 16

Cesium carbonate (163 mg, 0.50 mmol), bis(acetonitrile)palladium (II) chloride (1.0 mg, 0.004 mmol) and XPhos (5.2 mg, 0.011 mmol) were combined in a 1 dram vial. The mixture was purged with nitrogen then 3-trifluoromethylbenzyl chloride (39 mg, 0.20 mmol) and a solution of alkyne 11 (100 mg, 0.24 mmol) in MeCN (0.5 mL) were added sequentially. The vial was sealed under nitrogen and heated at 85° C. overnight. The mixture was then cooled, diluted with EtOAc and filtered through celite. The filtrate was concentrated in vacuo. Purification of the crude residue two times by flash column chromatography on 12 g silica gel (hexanes→EtOAc, gradient) afforded 79 mg (69%) of allene 16.

Step 2. Deprotection of 16 to Give 17

In accordance with the procedures of example 3, step 2, THP ether 16 (79 mg, 0.14 mmol) was converted into 49 mg (73%) of 17.

Step 3. Hydrogenation of 17 to Give 18

Allene 17 (10 mg, 0.02 mmol) was dissolved in ethanol and converted into 3 mg (30%) of saturated compound 18 using an H-Cube hydrogenation reactor from Thalesnano, Inc, using a Pd/C catalyst cartridge.

Step 4. Saponification of 18 to Give 19

Lithium hydroxide (0.1 mL of a 1.0 M aqueous solution, 0.1 mmol) was added to a solution of 18 (3 mg, 0.006 mmol) in THF (0.1 mL). After stirring 2 days at room temperature, the mixture was acidified with 1 N HCl (0.2 mL) and extracted with $CH_2Cl_2$ (10 mL). The organic phase was washed with brine (1 mL) then dried ($MgSO_4$), filtered and concentrated in vacuo. Purification of the crude residue by flash column chromatography on 4 g silica gel ($CH_2Cl_2$→15% MeOH/$CH_2Cl_2$, gradient) afforded 2 mg (69%) of the title compound (19).

Example 6

5-(3-((1R,2R,3R,5R)-5-chloro-3-hydroxy-2-((R)-3-(3-(trifluoromethyl)phenyl)propa-1,2-dienyl)cyclopentyl)propyl)thiophene-2-carboxylic acid (20)

Lithium hydroxide (0.2 mL of a 1.0 M aqueous solution, 0.2 mmol) was added to a solution of 17 (from example 5, step 2, 20 mg, 0.041 mmol) in THF (0.2 mL). After stirring 3 days at room temperature, the mixture was acidified with 1 N HCl (0.3 mL) and extracted with $CH_2Cl_2$ (20 mL). The organic phase was dried ($MgSO_4$), filtered and concentrated in vacuo. Purification of the crude residue two times by flash column chromatography on 4 g silica gel ($CH_2Cl_2$→10% MeOH/$CH_2Cl_2$, gradient) afforded 17 mg (88%) of the title compound (20).

Example 7

5-(3-((1R,2R,3R,5R)-5-chloro-3-hydroxy-2-(3-phenylpropyl)cyclopentyl)propyl)thiophene-2-carboxylic acid (15c)

Step 1. Reaction of 11 with Benzyl Chloride to Give 12c

In accordance with the procedure of example 3, step 1, 11 (150 mg, 0.37 mmol) and benzyl chloride (39 μL, 0.34 mmol) were converted into 150 mg (88%) of 12c.

Step 2. Deprotection of 12c to Give 13c

In accordance with the procedures of example 3, step 2, THP ether 12c (120 mg, 0.24 mmol) was converted into 80 mg (80%) of 13c.

Step 3. Hydrogenation of 13c to Give 14c

In accordance with the procedures of example 3, step 3, alkyne 13c (40 mg, 0.096 mmol) was converted into 20 mg (50%) of saturated compound 14c.

Step 4. Saponification of 14c to Give 15c

Lithium hydroxide (0.4 mL of a 1.0 M aqueous solution, 0.4 mmol) was added to a solution of 14c (20 mg, 0.048 mmol) in THF (0.4 mL). After stirring overnight at room temperature, the mixture was acidified with 1 N HCl (0.5 mL) and extracted with $CH_2Cl_2$ (20 mL). The organic phase was washed with brine (1 mL) then dried ($MgSO_4$), filtered and concentrated in vacuo. Purification of the crude residue by flash column chromatography on 4 g silica gel ($CH_2Cl_2 \rightarrow$ 10% $MeOH/CH_2Cl_2$, gradient) afforded 14 mg (72%) of the title compound (15c).

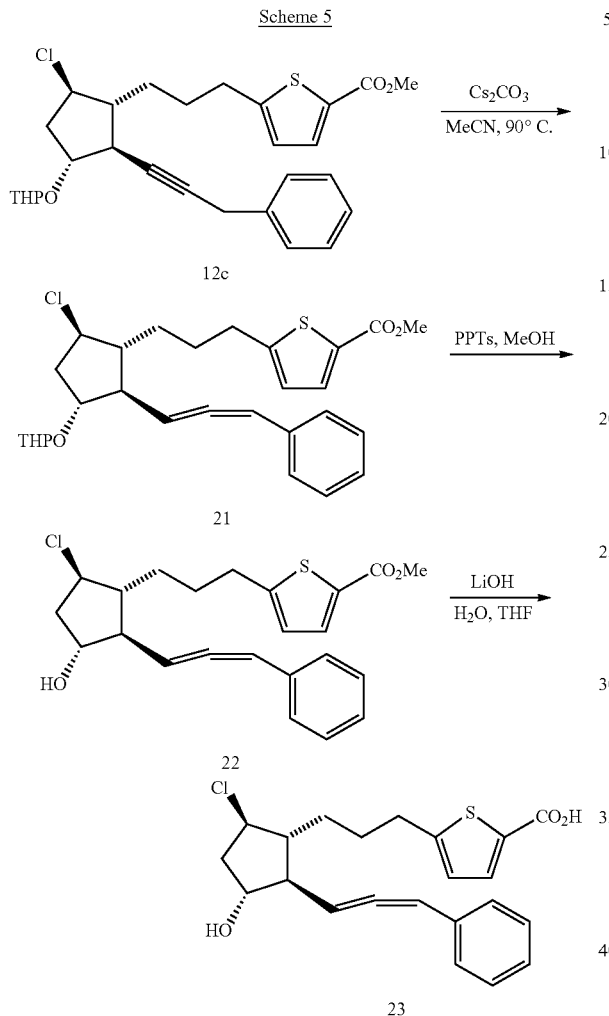

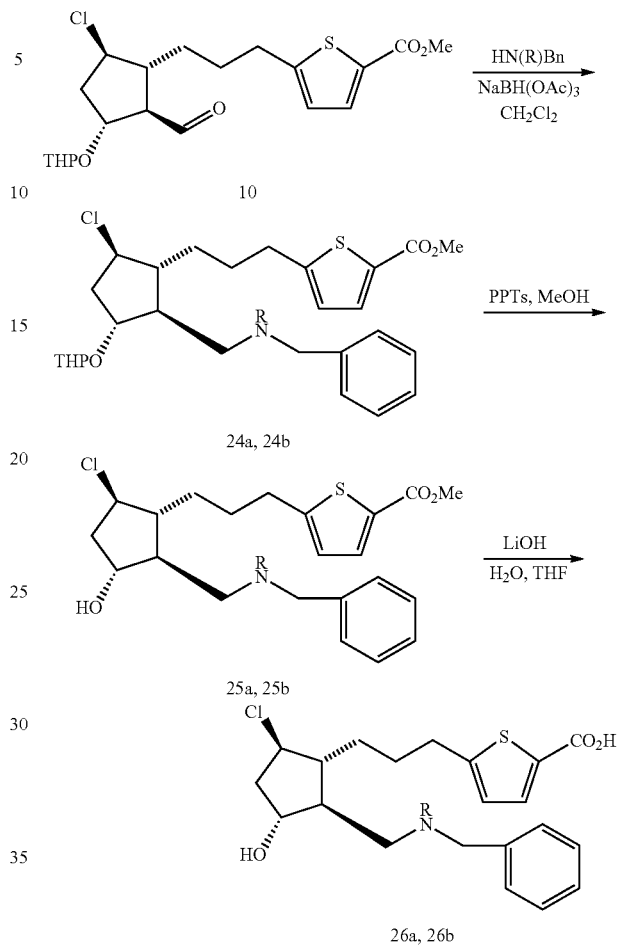

Example 8

5-(3-((1R,2R,3R,5R)-5-chloro-3-hydroxy-2-((R)-3-phenylpropa-1,2-dienyl)cyclopentyl)propyl)thiophene-2-carboxylic acid (23)

Step 1. Reaction of 12c to Give 21

Cesium carbonate (82 mg, 0.25 mmol) was added to a solution of alkyne 12c (from example 7, step 1, 50 mg, 0.10 mmol) in MeCN (0.3 mL) in a 1 dram vial. The vial was sealed and heated at 90° C. After 18 h, the mixture was cooled and filtered through celite. The filtrate was concentrated in vacuo to afford 45 mg (90%) of allene 21.

Step 2. Deprotection of 21 to Give 22

In accordance with the procedures of example 3, step 2, THP ether 21 (45 mg, 0.09 mmol) was converted into 10 mg (27%) of 22.

Step 3. Saponification of 22 to Give 23

In accordance with the procedures of example 7, step 4, ester 22 (10 mg, 0.024 mmol) was converted into 2 mg (21%) of the title compound (23).

Example 9

5-(3-((1R,2S,3R,5R)-2-((benzyl(methyl)amino)methyl)-5-chloro-3-hydroxycyclopentyl)propyl)thiophene-2-carboxylic acid (26a)

Step 1. Reduction Amination to Give 24a

A solution of aldehyde 10 (see preparation 2, step 1, 0.437 mmol) in $CH_2Cl_2$ (3.5 mL) was added to a vial charged with N-methylbenzylamine (0.874 mmol) and the resulting solution was agitated on an orbital shaker at room temperature for 1.5 h. $NaBH(OAc)_3$ (190 mg, 0.874 mmol) was added and the reaction mixture was agitated on an orbital shaker at room temperature for a further 16 h. Saturated aqueous $NaHCO_3$ solution (3 mL) was added and the resulting solution extracted with $CH_2Cl_2$ (2×4 mL). The combined organic phase was concentrated in vacuo to yield crude intermediate 24a, which was used in the next step without further purification.

Step 2. Deprotection of 24a to Give 25a

Crude intermediate 24a (0.437 mmol theoretical) was dissolved in MeOH (1 mL) and decanted into a 4-mL vial. A solution of TsOH (91 mg, 0.44 mmol, 1 eq.) in MeOH (1 mL) was added and the resulting solution was agitated on an orbital shaker at room temperature for 40 h. Saturated aqueous $NaHCO_3$ solution (3 mL) was added and the resulting mixture extracted with DCM (2×4 mL). The combined organic extractions were concentrated in vacuo to yield intermediate 25a. The intermediate was used in the next step without further purification.

Step 3. Saponification of 25a to Give 26a

Lithium hydroxide (2 mL of a 1.0 aqueous solution, 2.0 mmol) was added to a solution of the crude intermediate 25a (assumed to be 0.437 mmol) in MeOH (8 mL). The resulting solution was agitated on an orbital shaker at room temperature for 110 h. The pH of the reaction was adjusted to less than 7 by addition of aqueous 2 M HCl solution (0.8 mL) and the reaction mixture was then concentrated in vacuo to yield an oil suspended in residual water. The water was decanted, the residue dissolved in DMSO (3 mL), and DSMO solution filtered. Product x was purified by reversed phase preparative HPLC eluting with 0.1% formic acid in HPLC grade water and acetonitrile to afford 84.5 mg (46% over 3 steps) of the title compound (26a).

Example 10

5-(3-((1R,2S,3R,5R)-2-((benzylamino)methyl)-5-chloro-3-hydroxycyclopentyl)propyl)thiophene-2-carboxylic acid (26b)

In accordance with the procedures of example 9, benzylamine and aldehyde 10 were converted into 23 mg (13%) of the title compound (26b) after using 60 mM ammonium carbonate and neat acetonitrile for the reverse phase preparative HPLC purification.

Preparation 2

Methyl 5-(3-((1R,2S,3R,5R)-5-chloro-2-ethynyl-3-(tetrahydro-2H-pyran-2-yloxy)cyclopentyl)propyl)thiophene-2-carboxylate (11)

Step 1. Oxidation of 5 to Give 10

DMSO (177 µL, 2.5 mmol) was added to a solution of oxalyl chloride (600 µL of a 2.0 M solution in $CH_2Cl_2$, 1.2 mmol) in $CH_2Cl_2$ (8.5 mL) at −78° C. After 15 min, a solution of alcohol 5 (417 mg, 1.0 mmol) in $CH_2Cl_2$ (2.9 mL) was added via cannula. After 15 min at −78° C., triethylamine (1.11 mL, 8.0 mmol) was added and the reaction was allowed to warm to 0° C. After 1.5 h at 0° C., the reaction mixture was diluted with saturated aqueous $NaHCO_3$ (50 mL) and extracted with $CH_2Cl_2$ (3×70 mL). The combined extracts were washed with brine (50 mL), dried ($Na_2SO_4$), filtered and concentrated in vacuo to afford aldehyde 10, which was used without further purification.

Step 2. Reaction of 10 to Give 11 (in Accordance with the Procedures of Roth, et al., *Synthesis* 2004, 59-62).

To a mixture of tosyl azide (240 mg, 1.22 mmol) and potassium carbonate (415 mg, 3.0 mmol) in MeCN (15 mL) was added dimethyl-2-oxopropylphosphonate (166 µL, 1.20 mmol). After 2 h of stirring at room temperature, a solution of crude aldehyde 10 from step 1 (~1.0 mmol) in MeOH (3 mL) was added by cannula. The mixture was allowed to stir overnight at room temperature then was concentrated in vacuo. Water (10 mL) was added and the mixture was extracted with EtOAc (20 mL). The organic phase was washed with water (10 mL) and brine (10 mL), then dried ($Na_2SO_4$), filtered and concentrated in vacuo. Purification of the crude residue by chromatography on 40 g silica gel (hexanes→EtOAc, gradient) afforded 203 mg (49%, slightly contaminated with tosyl amide) of the title compound (11).

In vitro Testing

US 2007/0129552, incorporated by reference herein, describes the methods used to obtain the in vitro data in the table below.

TABLE 1

| Structure | EP2 data | | | EP4 data | | Other Receptors (EC50 in nM) | | | | | |
|---|---|---|---|---|---|---|---|---|---|---|---|
| | flipr EC50 | cAMP EC50 | Ki | flipr EC50 | KI | hFP | hEP1 | hEP3A | hTP | hIP | hDP |
| (structure 1) | 195 | 5 | 214 | 2333 | 3172 | 22546 | 97 | 88 | 11 | 7 | >10000 |
| (structure 2) | 255 | 0.5 | 3 | 6535 | 606 | NA | NA | NA | 2524 | NA | >10000 |

TABLE 1-continued

| Structure | EP2 data | | | EP4 data | | Other Receptors (EC50 in nM) | | | | | |
|---|---|---|---|---|---|---|---|---|---|---|---|
| | flipr EC50 | cAMP EC50 | Ki | flipr EC50 | KI | hFP | hEP1 | hEP3A | hTP | hIP | hDP |
| (structure) | 9917 | 1 | 0.6 | 10069 | 999 | NA | NA | 8063 | 7114 | NA | NA |
| (structure) | 13783 | 0.9 | 4 | >10000 | 1845 | NA | NA | NA | NA | NA | NA |
| (structure) | 2519 | 0.3 | 0.5 | | 740 | NA | 4256 | | | NA | NA |
| (structure) | 3262 | 1.7 | 11 | | | NA | NA | NA | NA | NA | NA |
| (structure) | | 0.6 | 3 | 4958 | 2162 | NA | NA | | | NA | 6781 |
| (structure) | | 1.7 | 6 | 11075 | 715 | NA | NA | NA | NA | NA | 10245 |

TABLE 1-continued

| Structure | EP2 data | | | EP4 data | | Other Receptors (EC50 in nM) | | | | | |
| --- | --- | --- | --- | --- | --- | --- | --- | --- | --- | --- | --- |
| | flipr EC50 | cAMP EC50 | Ki | flipr EC50 | KI | hFP | hEP1 | hEP3A | hTP | hIP | hDP |
| 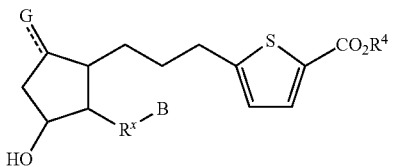 | | 3.6 | 24 | | NA | NA | NA | NA | NA | NA | 5617 |
| 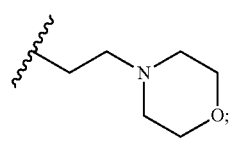 [SMILES: *CCN1CCOCC1] | | 6 | 143 | | NA | NA | NA | NA | NA | NA | NA |

The foregoing description details specific methods and compositions that can be employed to practice the present invention, and represents the best mode contemplated. However, it is apparent for one of ordinary skill in the art that further compounds with the desired pharmacological properties can be prepared in an analogous manner, and that the disclosed compounds can also be obtained from different starting compounds via different chemical reactions. Similarly, different pharmaceutical compositions may be prepared and used with substantially the same result. Thus, however detailed the foregoing may appear in text, it should not be construed as limiting the overall scope hereof; rather, the ambit of the present invention is to be governed only by the lawful construction of the appended claims.

What is claimed is:

1. A compound represented by a formula:

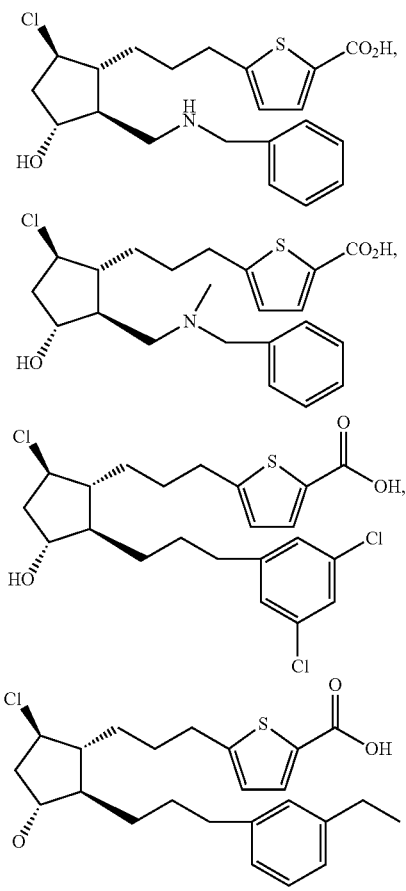

wherein a dashed line represents the presence or absence of a bond;

G is —H, —Cl, —F, or —CN;

$R^x$ is —(CH$_2$)$_3$—, —CH=CHCH$_2$—, —CH=C=CH—, —CH$_2$OCH$_2$—, —CH$_2$SCH$_2$—, —CH$_2$NHCH$_2$—, —(CH$_2$)$_2$N(CH$_3$)—, —(CH$_2$)$_2$O—, or —(CH$_2$)$_2$S—;

$R^4$ is —H, —CH$_3$, —CH$_2$OH, —(CH$_2$)$_2$OH, —CH$_2$CH=CH$_2$, or and

B is phenyl substituted with from 0 to 4 substituents, each selected from C$_{2-8}$ alkyl, C$_{1-8}$ —O-alkyl, C$_{1-8}$ hydroxyalkyl, —OH, —F, —Cl, —Br, or —CF$_3$.

2. The compound of claim 1, selected from:

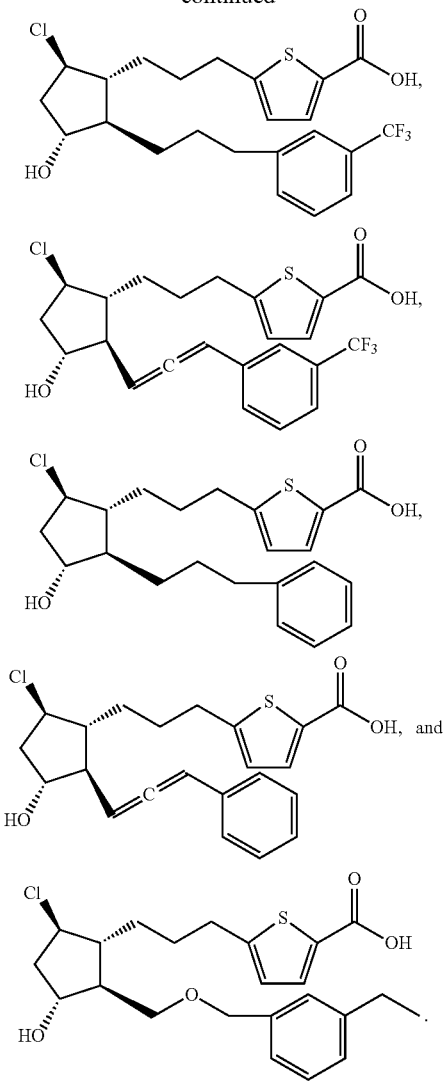
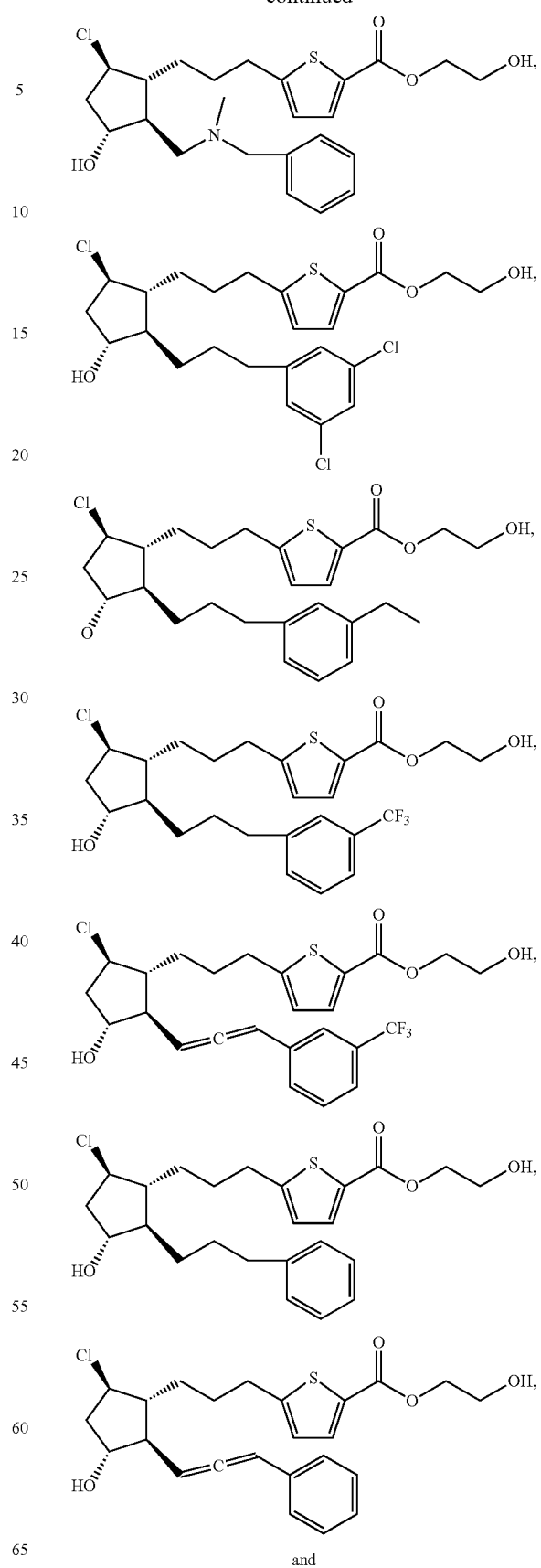
3. The compound of claim 1 wherein $R^4$ is:
—$(CH_2)_2OH$ or
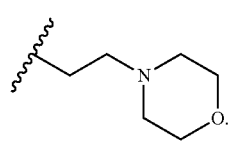 [SMILES: *CCN1CCOCC1]
4. The compound of claim 3 selected from:
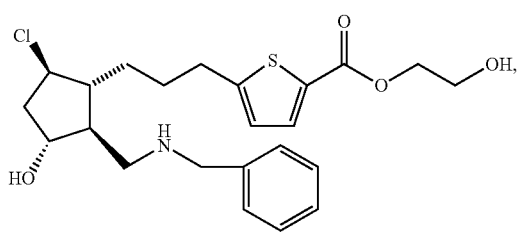
and -continued
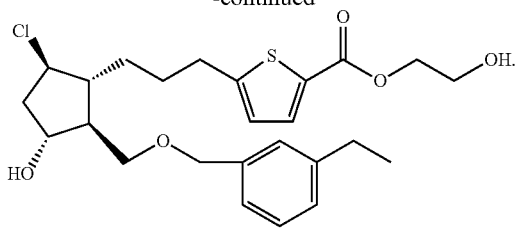
5. A method of reducing intraocular pressure, treating glaucoma or intraocular pressure, growing hair, or improving the appearance of hair, comprising administering the compound of claim 1 to a mammal in need thereof.
* * * * *